(12) United States Patent
Camelio et al.

(10) Patent No.: US 11,104,641 B2
(45) Date of Patent: Aug. 31, 2021

(54) BISCARBODIIMIDES AND POLYCARBODIIMIDES AND METHOD FOR THEIR PREPARATION

(71) Applicant: Dow Global Technologies LLC, Midland, MI (US)

(72) Inventors: Andrew M. Camelio, Midland, MI (US); Arkady L. Krasovskiy, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 33 days.

(21) Appl. No.: 16/078,643

(22) PCT Filed: Mar. 8, 2017

(86) PCT No.: PCT/US2017/021385
§ 371 (c)(1),
(2) Date: Aug. 22, 2018

(87) PCT Pub. No.: WO2017/172313
PCT Pub. Date: Oct. 5, 2017

(65) Prior Publication Data
US 2019/0023652 A1    Jan. 24, 2019

Related U.S. Application Data

(60) Provisional application No. 62/315,897, filed on Mar. 31, 2016.

(51) Int. Cl.
*C07C 267/00* (2006.01)
*B01J 27/236* (2006.01)
*B01J 27/25* (2006.01)

(52) U.S. Cl.
CPC .......... *C07C 267/00* (2013.01); *B01J 27/236* (2013.01); *B01J 27/25* (2013.01); *B01J 2523/11* (2013.01); *B01J 2523/13* (2013.01); *B01J 2523/14* (2013.01); *B01J 2523/15* (2013.01); *B01J 2523/16* (2013.01); *B01J 2523/18* (2013.01); *B01J 2523/21* (2013.01); *B01J 2523/22* (2013.01); *B01J 2523/23* (2013.01); *B01J 2523/24* (2013.01); *B01J 2523/25* (2013.01); *B01J 2523/26* (2013.01); *C07C 2601/16* (2017.05); *C07C 2603/74* (2017.05)

(58) Field of Classification Search
None
See application file for complete search history.

(56) References Cited

U.S. PATENT DOCUMENTS

| | | | |
|---|---|---|---|
| 3,725,404 A * | 4/1973 | Kuch | C07D 265/18 544/90 |
| 3,776,882 A | 12/1973 | Glanzstoff | |
| 3,972,933 A | 8/1976 | Lawton | |
| 5,464,890 A | 11/1995 | Diaz-Kotti et al. | |
| 5,635,298 A | 6/1997 | Delker | |
| 5,648,152 A | 7/1997 | Diaz-Kotti et al. | |
| 5,686,552 A | 11/1997 | Masuda et al. | |
| 5,700,881 A | 12/1997 | Wagner et al. | |
| 5,885,709 A | 3/1999 | Wick et al. | |
| 5,910,363 A | 6/1999 | Rogers et al. | |
| 6,537,979 B1 | 3/2003 | Kuo et al. | |
| 6,884,788 B2 | 4/2005 | Bulpitt et al. | |

FOREIGN PATENT DOCUMENTS

| | | | |
|---|---|---|---|
| CA | 02025418 A1 | | 3/1991 |
| CN | 104262199 | * | 1/2015 |
| DE | 924751 C | | 3/1955 |
| GB | 1065767 A | | 4/1967 |
| WO | 9402517 A1 | | 2/1994 |
| WO | 96/04422 A1 | | 2/1996 |

OTHER PUBLICATIONS

Thiourea (https://en.wikipedia.org/wiki/Thiourea) 2020. (Year: 2020).*
English Translation of Liu et al. (CN 104262199) 2015 (Year: 2015).*
Examination Report pertaining to corresponding European Patent Application No. 17713524.1, dated Dec. 4, 2019.
Iwakura, Y. and Noguchi, K. "Stable Biscarbodiimides." Bulletin of the Chemical Society of Japan 1967, 40, 2383-2388.
Zhang, W. and Sita, L. R. "Investigation of Dynamic Intr- and Intermolecular Processes within a Tether-Length Dependent Series of Group 4 Bimetallic Initiators for Stereomodulated Degenerative Transfer Living Ziegler-Natta Propene Polymerization." Advanced Synthesis and Catalysis 2008, 350, 439-447.
Babcock, J. R.; Incarvito, C.; Rheingold, A. L.; Fettinger, J. C.; and Sita, L. R.. Double hetocumulene metathesis of cyclic bis(trimethylsilylamido)stannylenes and tethered bimetallic bisamidinates from the resulting $\alpha,\omega$-biscarbodiimides. Organometallics 1999, 18, 5729-5732.
Bayram, M.; Blaser, D.; Wolper, C.; and Schulz, S. "Syntheses and Structures of Bis-Amidinate-Alane Complexes." Organometallics 2014, 33, 2080-2087.
Babcock, J. R. and Sita, L. R.. Facile preparation of unsymmetric carbodiimides via in situ Tin(II) mediated heterocummulene metathesis. Journal of American Chemical Society 1998, 120, 5585-5586.

(Continued)

*Primary Examiner* — Sudhakar Katakam
*Assistant Examiner* — Jennifer C Sawyer
(74) *Attorney, Agent, or Firm* — Dinsmore & Shohl LLP

(57) ABSTRACT

The present disclosure describes a method of synthesizing carbodiimides comprising providing an alkylisothiourea, providing a thiophilic reagent to the reaction mixture and reacting under conditions sufficient to provide the carbodiimide, and wherein the carbodiimide is a polycarbodiimide or a biscarbodiimide. The present disclosure further describes methods for isolating the carbodiimides. The present disclosure additionally describes isolated carbodiimide compositions.

8 Claims, No Drawings

(56) References Cited

OTHER PUBLICATIONS

Mccarty, C. G.; Parkinson, J. E.; and Wieland, D. M. "Elimination of methyl mercaptan from N-Substituted N'-cyano-S-methylisothioureas. Evidence for N-cyanocarbodiimides." The Journal of Organic Chemistry 1970, 35, 6, 2067-2069.

Ferris, A. F. and Schutz, B. A. "The preparation of carbodiimides, isocyanates, and isothiocyanates by metal ion-assisted elimination of mercaptan." Journal of Organic Chemistry 1963, 28, 71-74.

Sheehan, J.; Cruickshank, P.; and Boshart, G. "A convenient synthesis of water-soluble carbodiimides." The Journal of Organic Chemistry 1961, 26, 2525-2528.

Ali, A. R.; Ghosh, H.; and Patel, B. K. "A greener synthetic protocol for the preparation of carbodiimide." Tetrahedron Letters 2010, 51, 1019-1021.

Schlama, T.; Gouverneur, V.; and Mioskowski, C. "A new and efficient preparation of carbodiimides from ureas using dimethylphosgeniminium chloride as a dehydrating agent." Tetrahedron Letters 1996, 37, 39, 7047-7048.

Barvain, M. R.; Showalter, H. D. H.; and Doherty, A. M. "Preparation of N,N'-Bis(aryl)guanidines from Electron Deficient Amines via Masked Carbodiimides." Tetrahedron Letters 1997, 38 (39), 6799-6802.

Yamamoto, N. and Isobe, M. "Direct preparation of guanidine from trichloroacetamide. A potentially important method to (=)-Tetrodotoxin." Chemistry Letters 1994, 2299-2302.

Ma, D.; Xia, C.; Jiang, J.; Zhang, J.; Tang, W. "Aromatic nucleophilic substitution or CuI catalyzed coupling route to martinellic acid." The Journal of Organic Chemistry 2003, 68, 442-451.

Fleming, J. J., Fiori, K W.; Du Bois, J. "Novel Iminium Ion Equivalents Prepared through C—H Oxidation for the Stereocontrolled Synthesis of Functionalized Propargylic Amine Derivatives." J. Am. Chem. Soc. 2003, 125, 2028-2029.

Fleming, J. J.,McReynolds, M. D.; Du Bois, J. "(+)-Saxitoxin: A First and Second Generation Stereoselective Synthesis." J. Am. Chem. Soc. 2007, 129, 9964-9975.

Ermolat'ev, D. S., Bariwal, J. B., Steenackers, H. P. L.., De Keersmaecker, S. C. J., "Concise and Diversity-Oriented Route toward Polysubstituted 2-Aminoimidazole Alkaloids and Their Analogues." Angewandte Chemie. 2010, 1-62.

Holloway, P. C.; Merriam, K. P.; Etsell, T. H., Hydrometalurgy 2004, 74, 213-220.

Budhathoki-Uprety, J.; Reuther, J. F.; Novak, B. M. "Determining the regioregularity in alkyne polycarbodiimides and their orthogonal modification of side chains to yield perfectly alternating functional polymers." Macromolecules 2012, 45, 8155-8165.

Jin, G.; Jones, C.; Junk, P. C.; Lippert, K-A.; Rose, R. P.; and Stasch, A. "Synthesis and characterization of bulky guanidines and phosphaguanidines: precursors for low oxidation state metallacycles." New Journal of Chemistry 2009, 33, 64.

Pearson, A. D. "Approaches towards the synthesis of saxitoxin alkaloids." Doctoral Thesis 2013, Colorado State University.

PCT/US2017/021385, International Search Report and Written Opinion dated May 22, 2017.

PCT/US2017/021385, International Preliminary Report on Patentability dated Oct. 2, 2018.

Marquard et al., "Interaction and Activation of Carbon-Heteroatom $\pi$ Bonds with a Zr/Co Heterobimetallic Complex", Organometallics, 2014, 33, 2071-2079.

\* cited by examiner

BISCARBODIIMIDES AND POLYCARBODIIMIDES AND METHOD FOR THEIR PREPARATION

BACKGROUND

Carbodiimides are known for being versatile synthetic reagents for a variety of dehydrative chemical transformations, including the formation of esters from alcohols and acids, amides from amines and acids, anhydrides from acids, lactones from hydroxyl acids, and lactams from amino acids.

Carbodiimides are prepared from various precursors, such as ureas, thioureas, isocyanates, and isothioureas.

Uses of carbodiimides include, for example, as reactive intermediates in the synthesis of various organic functional groups, as in the addition of carbon nucleophiles to carbodiimides to afford amidines as chelating ligands.

It is known that carbodiimides and in particular molecules containing multiple carbodiimide groups are quite unstable, and very few discrete biscarbodiimides or polycarbodiimides have been reported. With few exceptions, the reported syntheses of biscarbodiimides and polycarbodiimides involve the immediate, in situ consumption of the carbodiimide without its isolation or purification. This is due to the previously mentioned instability of biscarbodiimides and polycarbodiimides to decomposition or rearrangement to monocarbodiimide during isolation and purification. Given the few options for preparing biscarbodiimides and polycarbodiimides and the limited structural diversity available by the known methods, it would be useful to have a method to prepare biscarbodiimides and polycarbodiimides. It would further be useful to have a method to isolate pure biscarbodiimides and polycarbodiimides.

SUMMARY OF THE INVENTION

The present disclosure describes a method of synthesizing carbodiimides comprising providing an alkylisothiourea, providing a thiophilic reagent to the reaction mixture and reacting under conditions sufficient to provide the carbodiimide, and wherein the carbodiimide is a polycarbodiimide or a biscarbodiimide.

The present disclosure further describes methods for isolating the carbodiimides.

The present disclosure additionally describes isolated carbodiimide compositions.

DETAILED DESCRIPTION

The present disclosure describes a method of preparing biscarbodiimides and polycarbodiimides. In one aspect, the present disclosure describes the treatment of isothioureas with silver nitrate and triethylamine in acetonitrile to provide the biscarbodiimides or polycarbodiimides. In another aspect, the biscarbodiimides or polycarbodiimides have been isolated by several sequences of dilution with hexanes, filtration of the mixture through diatomaceous silica, and evaporation.

Unless otherwise indicated, numeric ranges, for instance "from 2 to 10" or "$C_2$-$C_{10}$" are inclusive of the numbers defining the range (e.g., 2 and 10).

Unless otherwise indicated, ratios, percentages, parts, and the like are by weight.

As used herein, unless otherwise indicated, the phrase "molecular weight" refers to the number average molecular weight as measured in conventional manner.

"Alkyl," as used in this specification, whether alone or as part of another group (e.g., in dialkylamino), encompasses straight and branched chain aliphatic groups having the indicated number of carbon atoms, for example, ($C_5$-$C_{40}$) alkyl. If no number is indicated (e.g., aryl-alkyl-), then 1-20 alkyl carbons are contemplated. Preferred alkyl groups include, without limitation, methyl, ethyl, propyl, isopropyl, butyl, isobutyl, sec-butyl, tert-butyl, pentyl, neopentyl, cyclopentyl, hexyl, cyclohexyl, adamantyl, and tert-octyl.

The term "heteroalkyl" refers to an alkyl group as defined above with one or more heteroatoms (nitrogen, oxygen, sulfur, phosphorus) replacing one or more carbon atoms within the radical, for example, an ether or a thioether.

An "aryl" group refers to any functional group or substituent derived from an aromatic ring having the indicated number of carbon atoms, for example, ($C_3$-$C_{40}$)aryl. In one instance, aryl refers to an aromatic moiety comprising one or more aromatic rings. In one instance, the aryl group is a ($C_6$-$C_{18}$)aryl group. In one instance, the aryl group is a ($C_6$-$C_{10}$)aryl group. In one instance, the aryl group is a ($C_{10}$-$C_{18}$)aryl group. The aryl ring may be fused or otherwise attached to one or more heteroaryl rings, aromatic or non-aromatic hydrocarbon rings or heterocycloalkyl rings. Preferred aryls include, without limitation, phenyl, naphthyl, anthracenyl, and fluorenyl.

A "substituted aryl" group refers to an aryl group that is substituted with 1 or more substituents that are compatible with the syntheses described herein and having the indicated number of carbon atoms, for example, substituted ($C_3$-$C_{40}$) aryl. Such substituents include, but are not limited to, sulfonate groups, boron-containing groups, alkyl groups, nitro groups, halogens, cyano groups, carboxylic acids, esters, amides, ($C_2$-$C_8$)alkene, and other aromatic groups. Other substituents are known in the art. Unless otherwise indicated, the foregoing substituent groups are not themselves further substituted.

"Heteroaryl" refers to any functional group or substituent derived from an aromatic ring and containing at least one heteroatom selected from nitrogen, oxygen, and sulfur and having the indicated number of carbon atoms, for example, ($C_3$-$C_{40}$)heteroaryl. Preferably, the heteroaryl group is a five or six-membered ring. The heteroaryl ring may be fused or otherwise attached to one or more heteroaryl rings, aromatic or non-aromatic hydrocarbon rings or heterocycloalkyl rings. Examples of heteroaryl groups include, without limitation, pyridine, pyrimidine, pyridazine, pyrrole, triazine, imidazole, triazole, furan, thiophene, oxazole, thiazole. The heteroaryl group may be optionally substituted with one or more substituents that are compatible with the syntheses described herein and having the indicated number of carbon atoms, for example, substituted ($C_3$-$C_{40}$)heteroaryl. Such substituents include, but are not limited to, fluorosulfonate groups, boron-containing groups, ($C_1$-$C_8$)alkyl groups, nitro groups, halogens, cyano groups, carboxylic acids, esters, amides, ($C_2$-$C_8$)alkene and other aromatic groups. Other substituents are known in the art. Unless otherwise indicated, the foregoing substituent groups are not themselves further substituted.

"Aromatic compound" refers to a ring system having 4n+2 pi electrons where n is an integer.

"Thiophilic reagent" refers to a reagent suitable for reactive chemistry with the sulfur group of the isothiourea to enable the transformation to a carbodiimide.

As used herein, the term "($C_1$-$C_{40}$)hydrocarbyl" means a hydrocarbon radical of from 1 to 40 carbon atoms and the term "($C_1$-$C_{40}$)hydrocarbylene" means a hydrocarbon diradical of from 3 to 40 carbon atoms, wherein each hydrocarbon radical independently is aromatic (6 carbon atoms or more) or non-aromatic, saturated or unsaturated, straight chain or branched chain, cyclic (including mono- and polycyclic, fused and non-fused polycyclic, including bicyclic; 3 carbon atoms or more) or acyclic, or a combination of two or more thereof; and each hydrocarbon radical and diradical independently is the same as or different from another hydrocarbon radical and diradical, respectively, and independently is unsubstituted or substituted. Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, each of the aforementioned $(C_1-C_{40})$hydrocarbyl groups independently has a maximum of 40 carbon atoms. All individual values and subranges from 1 to 40 carbon atoms are included and disclosed herein; for example, the number of carbon atoms may range from an upper limit of 40, 30, 20, 15, 12 or 10 carbon atoms to a lower limit of 1, 5, 10, 14, 18 or 20 carbon atoms. For example each $(C_1-C_{40})$hydrocarbyl groups independently may be a $(C_1-C_{20})$hydrocarbyl), or in the alternative, a $(C_1-C_{12})$hydrocarbyl), or in the alternative, a $(C_5-C_{30})$hydrocarbyl), or in the alternative, a $(C_{10}-C_{35})$ hydrocarbyl) group. Examples of $(C_1-C_{40})$hydrocarbylene are unsubstituted or substituted $(C_6-C_{40})$arylene, $(C_3-C_{40})$cycloalkylene, and $(C_3-C_{40})$alkylene (e.g., $(C_3-C_{20})$alkylene). In some embodiments, the diradicals are on the terminal atoms of the hydrocarbylene as in a 1,3-alpha, omega diradical (e.g., —$CH_2CH_2CH_2$—) or a 1,5-alpha, omega diradical with internal substitution (e.g., —$CH_2CH_2CH(CH_3)CH_2CH_2$—). In other embodiments, the diradicals are on the non-terminal atoms of the hydrocarbylene as in a $C_7$ 2,6-diradical (e.g.,

or a $C_7$ 2,6-diradical with internal substitution (e.g.,

The term $(C_1-C_{40})$hydrocarbylene is also defined by having the two radicals of the diradical unit spaced apart by one or more intervening carbon atoms. The alpha, omega-diradical is a diradical that has maximum carbon backbone spacing between the radical carbons. Preferred is a 1,4-, 1,5-, or 1,6-diradical, and more preferably a 1,5-diradical. Also preferred is a 1,4-diradical, 1,5-diradical, or 1,6-diradical version of $(C_6-C_{18})$arylene, $(C_4-C_{20})$cycloalkylene, or $(C_3-C_{20})$alkylene.

As used herein, the term "$(C_1-C_{40})$heterohydrocarbyl" means a heterohydrocarbon radical of from 1 to 40 carbon atoms and the term "$(C_1-C_{40})$heterohydrocarbylene" means a heterohydrocarbon diradical of from 3 to 40 carbon atoms, and each heterohydrocarbon independently has one or more heteroatoms or heteroatomic groups 0; S; N; S(O); S(O)$_2$; S(O)$_2$N; Si(R$^C$)$_2$; Ge(R$^C$)$_2$; P(R$^C$); P(O)(R$^C$); and N(R$^C$), wherein independently each R$^C$ is unsubstituted $(C_1-C_{18})$ hydrocarbyl or an unsubstituted $(C_1-C_{18})$heterohydrocarbyl, or absent (e.g., absent when N comprises —N=). Each $(C_1-C_{40})$heterohydrocarbyl and $(C_1-C_{40})$heterohydrocarbylene independently is unsubstituted or substituted, aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another. Preferably, the $(C_1-C_{40})$heterohydrocarbyl independently is unsubstituted or substituted $(C_1-C_{40})$heteroalkyl, $(C_1-C_{40})$hydrocarbyl-O—, $(C_1-C_{40})$hydrocarbyl-S—, $(C_1-C_{40})$hydrocarbyl-S(O)—, $(C_1-C_{40})$hydrocarbyl-S(O)$_2$—, $(C_1-C_{40})$hydrocarbyl-SnR$^C$)$_2$—, $(C_1-C_{40})$hydrocarbyl-Ge(R$^C$)$_2$—, $(C_1-C_{40})$hydrocarbyl-N(R$^C$)—, $(C_1-C_{40})$hydrocarbyl-P(R$^C$)—, $(C_1-C_{40})$hydrocarbyl-P(O)(R$^C$)—, $(C_2-C_{40})$heterocycloalkyl, $(C_2-C_{19})$heterocycloalkyl-$(C_1-C_{20})$alkylene, $(C_3-C_{20})$cycloalkyl-$(C_1-C_{19})$heteroalkylene, $(C_2-C_{19})$heterocycloalkyl-$(C_1-C_{20})$heteroalkylene, $(C_1-C_{40})$heteroaryl, $(C_1-C_{19})$heteroaryl-$(C_1-C_{20})$alkylene, $(C_6-C_{20})$aryl-$(C_1-C_{19})$heteroalkylene, or $(C_1-C_{19})$heteroaryl-$(C_1-C_{20})$heteroalkylene.

The term "$(C_3-C_{40})$heteroaryl" means an unsubstituted or substituted mono-, bi- or tricyclic heteroaromatic hydrocarbon radical of from 3 to 40 total carbon atoms and from 1 to 5 heteroatoms, and the mono-, bi- or tricyclic radical comprises 1, 2 or 3 rings, respectively, wherein the 2 or 3 rings independently are fused or non-fused and at least one of the 2 or 3 rings is heteroaromatic. Other heteroaryl groups (e.g., $(C_3-C_{12})$heteroaryl)) are defined in an analogous manner. The monocyclic heteroaromatic hydrocarbon radical is a 5-membered or 6-membered ring. The 5-membered ring has from 1 to 4 carbon atoms and from 4 to 1 heteroatoms, respectively, each heteroatom being O, S, N, or P, and preferably O, S, or N. Examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 3, 4 or 5 carbon atoms and 3, 2 or 1 heteroatoms, the heteroatoms being N or P, and preferably N. Examples of 6-membered ring heteroaromatic hydrocarbon radical are pyridine-2-yl; pyrimidin-2-yl; and pyrazin-2-yl. The bicyclic heteroaromatic hydrocarbon radical preferably is a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical preferably is a fused 5,6,5-; 5,6,6-; 6,5,6-; or 6,6,6-ring system. An example of the fused 5,6,5-ring system is 1,7-dihydropyrrolo[3,2-f]indol-1-yl. An example of the fused 5,6,6-ring system is 1H-benzo[f]indol-1-yl. An example of the fused 6,5,6-ring system is 9H-carbazol-9-yl. An example of the fused 6,5,6-ring system is 9H-carbazol-9-yl. An example of the fused 6,6,6-ring system is acrydin-9-yl.

The terms [(C+Si)$_3$-(C+Si)$_{40}$] organosilylene and [(C+Ge)$_3$-(C+Ge)$_{40}$] organogermylene are defined as diradicals in which the two radical bearing atoms of the diradical unit are spaced apart by one or more intervening carbon, silicon and/or germanium atoms. Such [(C+Si)$_3$-(C+Si)$_{40}$] organosilylene and [(C+Ge)$_3$-(C+Ge)$_{40}$] organogermylene groups can be substituted or unsubstituted. In some embodiments the diradicals are on the terminal atoms of the organosilylene or organogermylene as in a 1,5 alpha, omega diradical (e.g. —$CH_2CH_2Si(C_2H_5)_2CH_2CH_2$— and —$CH_2CH_2Ge(C_2H_5)_2CH_2CH_2$—). In other embodiments, the diradicals are on the non-terminal atoms of the organosilylene or organogermylene as in a substituted (C+Si)₇ 2,6-diradical

and a substituted (C+Ge)₇ 2,6-diradical ( ).

The term "$(C_1-C_{40})$alkylene" means a saturated or unsaturated straight chain or branched chain diradical of from 1 to 40 carbon atoms that is unsubstituted or substituted. Examples of unsubstituted $(C_1-C_{40})$alkylene are unsubstituted $(C_3-C_{20})$alkylene, including unsubstituted 1,3-$(C_3-C_{10})$alkylene; 1,4-$(C_4-C_{10})$alkylene; —$(CH_2)_3$—; —$(CH_2)_4$—; —$(CH_2)_5$—; —$(CH_2)_6$—; —$(CH_2)_7$—; —$(CH_2)_8$—; and —$(CH_2)_4CH(CH_3)$—. Examples of substituted $(C_1-C_{40})$alkylene are substituted $(C_3-C_{20})$alkylene; —$CF_2CF_2CF_2$—; and —$(CH_2)_{14}C(CH_3)_2(CH_2)_5$— (i.e., a 6,6-dimethyl substituted normal-1,20-eicosylene). Examples of substituted $(C_1-C_{40})$alkylene also include 1,2-bis(methylene)cyclopentane; 1,2-bis(methylene)cyclohexane; 2,3-bis(methylene)-7,7-dimethyl-bicyclo[2.2.1]heptane; and 2,3-bis(methylene)bicyclo[2.2.2]octane.

The term "$(C_3-C_{40})$cycloalkylene" means a cyclic diradical (i.e., the radicals are on ring atoms) of from 3 to 40 carbon atoms that is unsubstituted or substituted. Examples of unsubstituted $(C_3-C_{40})$cycloalkylene are 1,3-cyclobutylene, 1,3-cyclopentylene, and 1,4-cyclohexylene. Examples of substituted $(C_3-C_{40})$cycloalkylene are 2-trimethylsilyl-1, 4-cyclohexylene and 1,2-dimethyl-1,3-cyclohexylene.

As used herein, the definitions of the terms hydrocarbyl, heterohydrocarbyl, hydrocarbylene, heterohydrocarbylene, alkyl, alkylene, heteroalkyl, heteroalkylene, aryl, arylene, heteroaryl, heteroarylene, cycloalkyl, cycloalkylene, heterocycloalkyl, heterocycloalkylene, organosilylene, organogermylene are intended to include every possible stereoisomer.

The present disclosure describes a process for preparing a biscarbodiimide by reaction of an alykylisothiourea with a thiophilic reagent in a reaction mixture. In one instance, the reaction mixture further comprises a solvent. In one instance, the reaction mixture further comprises a base. This process is shown generally in Formula (1):

(1)

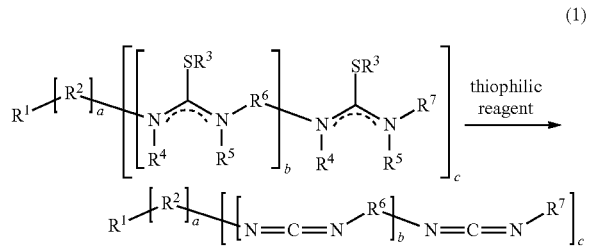

Where:
$R^1$=H; $(C_1-C_{40})$hydrocarbyl, $(C_1-C_{40})$heterohydrocarbyl;
$R^2$=$(C_1-C_{40})$hydrocarbylene, $(C_1-C_{40})$heterohydrocarbylene;
$R^3$=H; $(C_1-C_{40})$hydrocarbyl, $(C_1-C_{40})$heterohydrocarbyl;
$R^4$=H; or absent;
$R^5$=H; or absent;
$R^6$=$(C_1-C_{40})$hydrocarbylene, $(C_1-C_{40})$heterohydrocarbylene;
$R^7$=H; $(C_1-C_{40})$hydrocarbyl, $(C_1-C_{40})$heterohydrocarbyl;
a is 0 or 1;
b is from 0 to 10; and
c is from 1 to 10.

The compound shown to the left of the arrow in Formula (1) is an isothiourea. The isothiourea may alternatively be linear where a is 0 or may have a central core with branches extending therefrom where a is 1.

The compound shown to the right of the arrow in Formula (1) is a carbodiimide. The carbodiimide molecule may contain multiple carbodiimide moieties, alternatively connected linearly in which case a is 0 and the number of carbodiimide groups is the sum of b and c, or connected to a central core and not linearly in which case a is 1 and the number of carbodiimide groups is the product of b+1 and c. If there are a total of two carbodiimide groups then the molecule is termed a biscarbodiimide whereas if there are a total of more than two carbodiimide groups then the molecule is termed a polycarbodiimide.

As is shown in Formula (1), $R^2$ and $R^6$ are diradical, wherein each of these substituents serves as a bridge and is bonded to two other atoms of the molecule as is shown.

The dotted line linkage on the isothiourea in Formula (1) indicates that one of the two bonds adjacent the dotted line linkage is a double bond while the other is a single bond. One of $R^4$ or $R^5$ will be absent from the Nitrogen that includes the double bond.

In one instance, the reaction mixture includes a solvent, for example, acetonitrile, proprionitrile, butyronirile, isobutyronitrile, valeronitrile, hexanenitrile, trimethylacetonitrile, malonitrile, succionitrile, glutaronitrile, adiponitrile, 1,5-dicyanopentane, 1,6-dicyanohexane, N,N-dimethylformamide, N,N-dimethylacetamide, acetone, methylene chloride, 1,2-dichloroethane, chloroform, carbontetrachloride, 1,4-dioxane, benzene, toluene, xylenes, pentane, hexanes, heptanes, petroleum ether, diethyl ether, tetrahydrofuran, 2-methyltetrahydrofuran, methyl-t-butyl ether, or a mixture thereof.

The thiophilic reagent is selected to enable the conversion of the isothiourea to the carbodiimide. In one instance, the thiophilic reagent is a metal that is not an alkali metal. In one instance, the thiophilic reagent is a metal that is a transition metal. In one instance, the thiophilic reagent is selected from the group consisting of a halide, amine, nitrile, triflate, nitrate, acetate, acetylacetonate, carbonate, oxalate, oxide, phosphate, sulfite, or sulfate of copper, zinc, gold, molybdenum, mercury, tungsten, nickel, silver, iron, cobalt, and manganese. In one instance, the thiophilic reagent is selected from the group consisting of a halide, amine, nitrile, triflate, nitrate, acetate, acetylacetonate, carbonate, oxalate, oxide, phosphate, sulfite, or sulfate of silver. In one instance, the thiophilic reagent is silver nitrate.

In one instance, the reaction mixture includes a base, for example, acyclic or cyclic N,N,N-trisubstituted amine including, but not limited to, trimethylamine, triethylamine, N,N-diisopropylethyl amine, N,N,N',N'-tetramethylethylenediamine or TMEDA, N,N,N',N'-tetramethyl-1,3-propanediamine or TMPDA, N,N,N',N'-tetramethyl-1,4-butanediamine or TMBDA, N,N,N',N'-tetraethylethylenediamine or TMEEA, N,N,N',N'-tetraethyl-1,3-propanediamine or TMPEA, N,N,N',N'-tetramethyl-1,5-pentanediamine, N,N,N',N'-tetramethyl-1,6-hexanediamine, N-ethyldicyclohexylamine, 1,2,2,6,6-pentamethylpiperidine, N-methylpiperidine, N-ethylpiperidine, N-methylpyrrolidine, N-ethylpyrrolidine, N-methylmorpholine or 4-methylmorpholine, 4-ethylmorpholine, N,N'-1,4-dimethylpiperazine, 1,3,5-trimethylhexahydro-1,3,5-triazine, 1,3,5-triethylhexahydro-1,3,5-triazine, 1,3,5-triphenylhexahydro-1,3,5-triazine, 1,3,5-tribenzylhexahydro-1,3,5-triazine, 1,4-diazabicyclo[2.2.2]octane or DABCO, 1-azabicyclo[2.2.2]octane or Quinuclidine, 1,5-diazabicyclo[4.3.0]non-5-ene or DBN, 1,8-diazabicyclo[5.4.0]undec-7-ene or DBU, 7-methyl-1,5,7-triazabicyclo[4.4.0]dec-5-ene or MTBD, 2-t-butyl-1,1,3,3-tetramethylguanidine, N,N,N-triphenylamine, N,N,N-dimethylphenylamine, N,N,N-diphenylmethylamine, 1,8-bis(dimethylamino)naphthalene or Proton-Sponge; any heteroaromatic amine including, but not limited to, pyridine, 2,6-lutidine, 2,4-lutidine, 2,6-di-t-butylpyridine, 2,6-di-t-butyl-4-methylpyridine, 2,4,6-tri-t-butylpyridine, 2,4,6-tri-t-butylpyrimidine, 4-t-butylpyridine, N,N-dimethylaminopyridine or DMAP, pyrazine, pyridazine, pyrimidine, s-triazine, phthalazine, quinoline, isoquinoline, quinoxaline, acridine, 3,4-dihydroisoquinoline, 2,2'-bipyridine, 4,4'-bipyridine, 1,10-phenanthroline, neocuproine, 1,7-phenanthroline, 3,4,7,8-tetramethyl-1,10-phenanthroline, 1-methylimidazole, 1-butylimidazole, 1-ethylimidazole, 1-benzylimidazole, 1-octylimidazole, 1-phenylimidazole, 1-methylpyrazole, 1-phenylpyrazole; any Group 1 (alkali) or Group 2 (alkaline) earth metal salts including, but not limited to, lithium bicarbonate, sodium bicarbonate, potassium bicarbonate, rubidium bicarbonate, cesium bicarbonate, francium bicarbonate, beryllium bicarbonate, magnesium bicarbonate, calcium bicarbonate, strontium bicarbonate, barium bicarbonate, radium bicarbonate, lithium carbonate, sodium carbonate, potassium carbonate, rubidium carbonate, cesium carbonate, francium carbonate, beryllium carbonate, magnesium carbonate, calcium carbonate, strontium carbonate, barium carbonate, radium carbonate, or mixtures thereof.

The reaction mixture has an operating temperature during the synthesis protocol described herein. Preferably, the operating temperature is in the range of from −78 to 50° C. In one instance, the preferred operating temperature is in the range of from −50 to 40° C. In one instance, the preferred operating temperature is in the range of from −20 to 30° C. In one instance, the preferred operating temperature is in the range of from −10 to 30° C.

In one instance, the reaction mixture is housed in light-free environment.

In one instance, the synthesis protocol described herein is suitable for preparing a carbodiimide having one of the following structures:

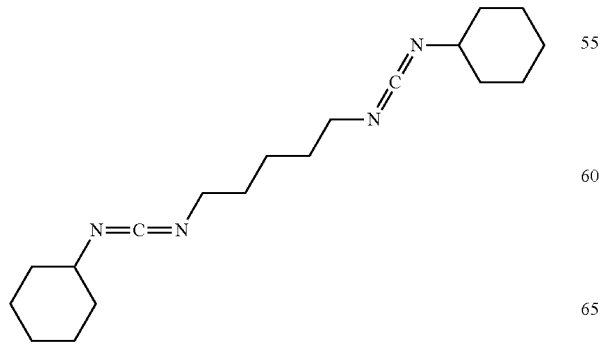

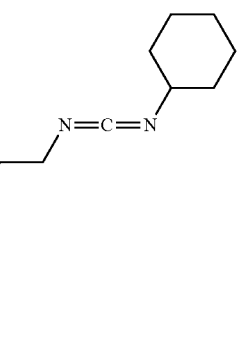

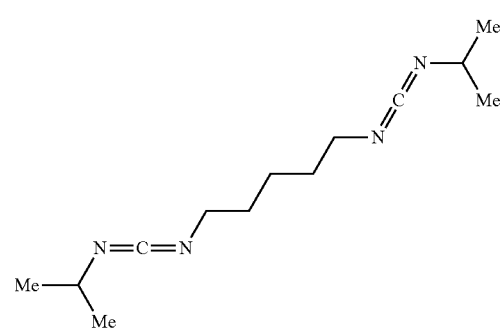

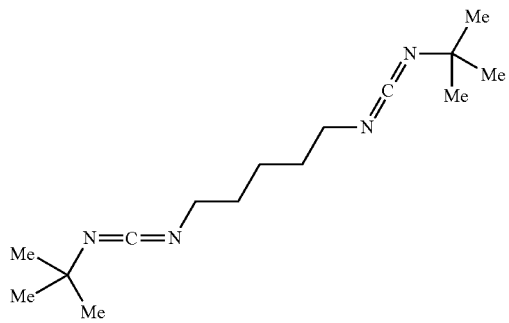

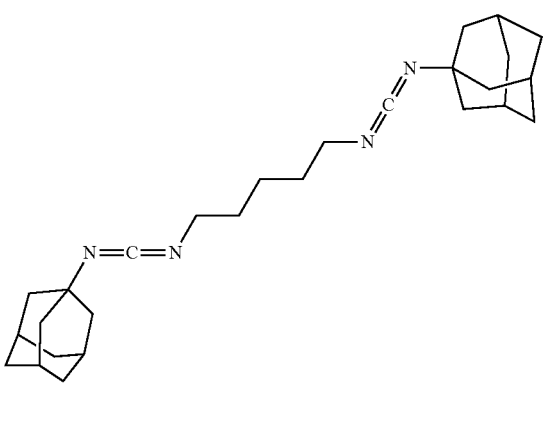

-continued

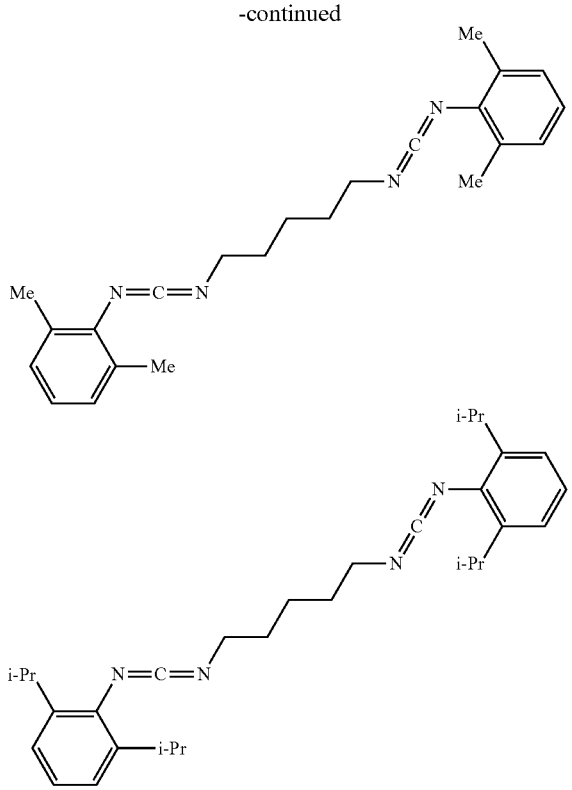

In one instance, the present disclosure describes a process for isolating a biscarbodiimide by a purification and isolation protocol involving one or more sequences of hexane dilution, filtration through diatomaceous silica, and evaporation. In one instance, the purification protocol comprises replacing the solvent used in the reaction mixture with hexanes. In one exemplary purification protocol, the reaction product of the synthesis of carbodiimides described herein is diluted with hexanes, stirred, suction filtered over a pad of diatomaceous silica (available under the trade name Celite) with hexanes, and concentrated. This purification process is repeated one or more times followed by suction filtering cold over a pad of diatomaceous silica with hexanes and concentrating in vacuo to provide the isolated carbodiimide. In one instance, the isolation protocol is sufficient to provide the carbodiimide product free of impurities within the limit of detection of proton NMR.

EXAMPLES

The following examples illustrate the present invention but are not intended to limit the scope of the invention.

Common abbreviations are listed below:

R, N, M, and X: as defined above;

Me: methyl; Ph: phenyl; i-Pr: iso-propyl; t-Bu: tert-butyl; Ts: toluene sulfonate; THF: tetrahydrofuran; Et$_2$O: diethyl ether; CH$_2$Cl$_2$: dichloromethane; CHCl$_3$: chloroform CCl$_4$: carbon tetrachloride; EtOH: ethanol; CH$_3$CN: acetonitrile; MeCN: acetonitrile; EtOAc: ethyl acetate; C$_6$D$_6$: deuterated benzene; Benzene-d$_6$: deuterated benzene; CDCl$_3$: deuterated chloroform; DMSO-d$_6$: deuterated dimethylsulfoxide; PPh$_3$: triphenylphosphine; NEt$_3$: triethylamine; MeI: methyl iodide; NaOH: sodium hydroxide; NaOCl: sodium hypochlorite; NaHCO$_3$: sodium bicarbonate; brine: saturated aqueous sodium chloride; Na$_2$SO$_4$: sodium sulfate; MgSO$_4$: magnesium sulfate; PCl$_5$: phosphorous pentachloride; Ph$_3$PBr$_2$: triphenylphosphine dibromide; Ph$_3$PCl$_2$: triphenylphosphine chloride; SOCl$_2$: Thionylchloride; AgNO$_3$: silver nitrate; N$_2$: nitrogen gas; PhMe: toluene; NMR: nuclear magnetic resonance; HRMS: high resolution mass spectrometry; LRMS: low resolution mass spectrometry; mmol: millimoles; mL: milliliters; M: molar; min: minutes; h: hours; d: days. NMR spectra were recorded on Varian 400-MR and VNMRS-500 spectrometers. $^1$H NMR data are reported as follows: chemical shift (multiplicity (br=broad, s=singlet, d=doublet, t=triplet, q=quartet, p=pentet, sex=sextet, sept=septet and m=multiplet), integration, and assignment). Chemical shifts for $^1$H NMR data are reported in ppm downfield from internal tetramethylsilane (TMS, δ scale) using residual protons in the deuterated solvent as references. $^{13}$C NMR data were determined with $^1$H decoupling, and the chemical shifts are reported in ppm versus tetramethylsilane.

The following comparative examples illustrate failed attempts at synthesizing biscarbodiimides using known techniques for synthesizing monocarbodiimides.

Comparative Example 1

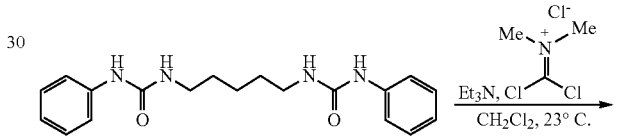

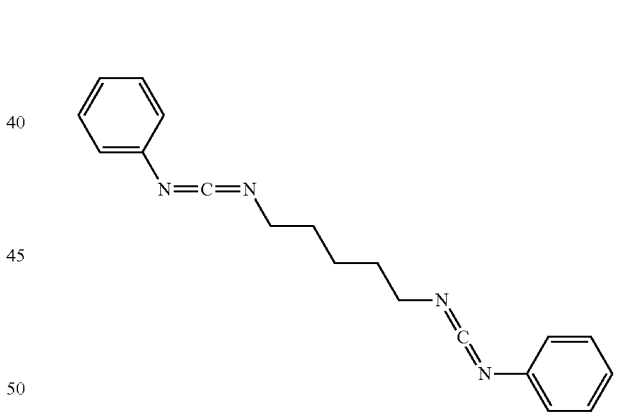

In a nitrogen filled glovebox to a suspension of the urea (20.0 mg, 0.059 mmol, 1.00 eq) and dimethylphosgeniminium chloride (9.5 mg, 0.059 mmol, 1.00 eq) in CH$_2$Cl$_2$ (1.0 mL) at 23° C. was added Et$_3$N (17.3 ul, 0.13 mmol, 2.10 eq). The heterogeneous mixture instantaneously became a golden yellow solution upon full addition of the Et$_3$N. After 10 minutes the solution was diluted with hexanes (5 mL), and the now white heterogeneous mixture was suction filtered to remove the triethylammonium hydrochloride, and concentrated. NMR (d-DMSO) of the filtrate solution (which is now a white solid) had shown no starting urea or desired product. A complex mixture of undesired products were observed as well as Me$_2$NCOCl. NMR of the filtered pale yellow solid had shown Et$_3$NHCl and Me$_2$NCOCl.

Comparative Example 2

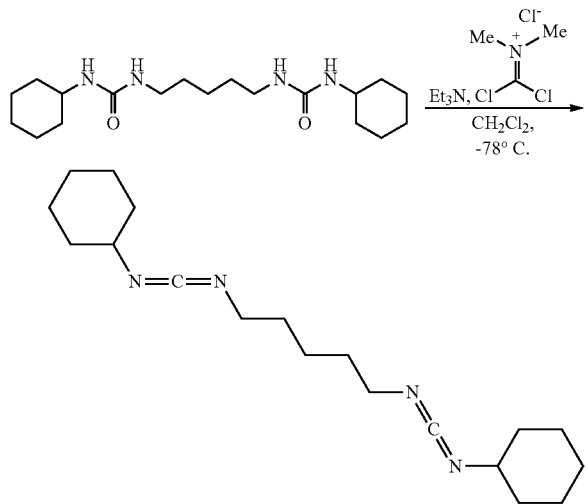

In a nitrogen filled glove box dimethylphosgeniminium chloride (22.5 mg, 0.14 mmol, 2.00 eq) was added to an ovendried flask and then was added the urea (24.5 mg, 0.07 mmol, 1.00 eq) followed by $CH_2Cl_2$ (2.0 mL) via syringe. The white suspension was sealed with a rubber septa, removed from the glovebox, immediately placed under nitrogen, and was placed into a bath cooled to −78° C., and stirred (500 rpm) for 30 mins. $Et_3N$ (20.8 mg, 15.2 ul, 0.15 mmol, 2.10 eq) was then added to the mixture in a quick dropwise manner via syringe. The heterogeneous mixture instantaneously became a golden yellow solution upon full addition of the $Et_3N$. After 10 minutes the solution was diluted with hexanes (5 mL), and the now white heterogeneous mixture was suction filtered to remove the triethylammonium hydrochloride, and concentrated. NMR ($CDCl_3$) of the filtrate solution (which is now a white solid) had shown no product, but what looks to be either polymerized material or destroyed material. NMR of the filtrate solid had shown no product, but what looks to be either polymerized material or destroyed material. NMR of the filtrate solution indicates the same result as well as the presence of $Et_3NHCl$.

Comparative Example 3

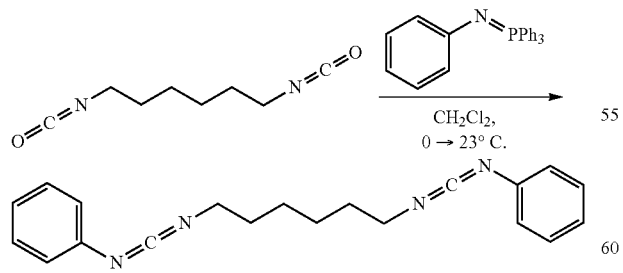

A solution of N-(Triphenylphosphoranylidene)aniline (150.0 mg, 0.42 mmol, 2.00 eq) in $CH_2Cl_2$ (2.5 mL) under nitrogen was placed in an ice water bath for 20 minutes upon which hexamethylene diisocyanate (25.3 mg, 39.0 ul, 0.21 mmol, 1.00 eq) was added neat via syringe. The clear colorless solution was allowed to stir (500 rpm) for 14 hrs warming gradually to 23° C. The clear colorless solution was diluted with hexanes (10 mL) and the resultant white mixture was concentrated to ~1 mL via rotary evaporation, further diluted with hexanes (10 mL), suction filtered over a pad of diatomaceous silica, and concentrated. NMR of the crude gum had shown product, along with a mixture of other products including triphenylphosphine oxide. NMR of filtrate solid had shown only TPPO and what looks to be decomposed material. Product is stable to silica gel according to 2-D TLC therefore the crude gum was attempted to be purified via silica gel chromatography using the ISCO; hexanes—10% EtOAc in hexanes followed by EtOAc flush. However, no product was isolated after the column, only mixed fractions with materials consistent with decomposition and triphenylphosphine oxide. Product is unstable to isolation using methods such as distillation, silica gel chromatography, as well as neutral or basic alumina chromatography.

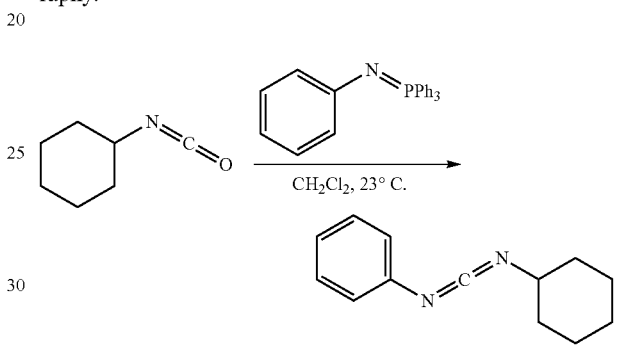

To a solution of N-(Triphenylphosphoranylidene)aniline (50.0 mg, 0.14 mmol, 1.00 eq) in $CH_2Cl_2$ (1.5 mL) was added cyclohexyl isocyanate (17.7 mg, 18.0 ul, 0.14 mmol, 1.00 eq). After 14 hrs the clear homogeneous solution was concentrated, diluted with hexanes (10 mL), suction filtered, and concentrated. NMR in $CDCl_3$ had shown practically pure product with some triphenylphosphine oxide remaining, as provided below. 2-D TLC (10% EA in hex) had shown that the compound was stable to silica gel so the crude foam was purified via silica gel chromatography; hexanes—10% EtOac in hexanes and then EtOAc flush to afford the carbodiimide product as a pale yellow oil (26.6 mg, 0.13 mmol, 95%). The product was isolated along with other minor impurities (TPPO). Product is stable to silica gel chromatography and distillation. NMR indicates product which contains residual triphenylphosphine oxide.

$R_f$=0.72 (10% EtOAc in hexanes)

$^1$H NMR (500 MHz, Chloroform-d) δ 7.28 (dd, J=13.7, 5.7 Hz, 2H), 7.09 (d, J=7.7 Hz, 3H), 3.48 (dq, J=10.4, 6.0, 4.9 Hz, 1H), 2.02 (dt, J=13.4, 5.8 Hz, 3H), 1.77 (dt, J=13.4, 4.3 Hz, 3H), 1.57-1.41 (m, 3H), 1.35 (td, J=16.4, 15.0, 8.3 Hz, 3H).

Comparative Example 4

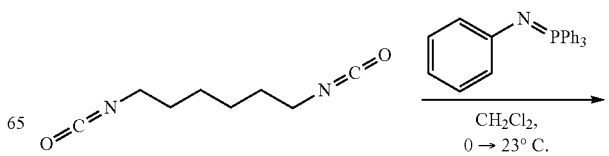

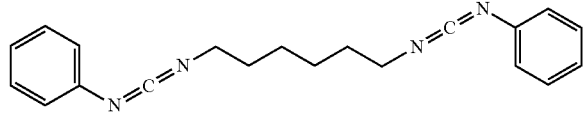

A solution of N-(Triphenylphosphoranylidene)aniline (297.0 mg, 0.84 mmol, 2.00 eq) in CH$_2$Cl$_2$ (5.0 mL) under nitrogen was placed in an ice water bath for 20 minutes upon which hexamethylene diisocyanate (70.6 mg, 67.5 ul, 0.42 mmol, 1.00 eq) was added neat via syringe. The clear colorless solution was allowed to stir (500 rpm) for 14 hrs at 23° C. The clear colorless solution was diluted with hexanes (10 mL) and the resultant white mixture was concentrated to ~1 mL via rotary evaporation, further diluted with hexanes (10 mL), suction filtered, and concentrated. NMR of the crude gum had shown desired product along with mono-carbodiimide/monoisocyanate adduct and TPPO. Resubmission of a portion of the crude material to an excess of N-(Triphenylphosphoranylidene)aniline returned no product; only decomposed material indicating the carbodiimide product is unstable to an excess of ylide. The unsubjected crude material was then suspended in pentane (20 mL), placed in a bath cooled to −78° C. for 1 hr, and suction filtered over a pad of diatomaceous silica using pentane chilled in an ice water bath. NMR of the concentrated material had shown product as well as TPPO remaining but still contained the mono-isocyanate adduct. Further purification was attempted using silica gel (neutralized with 5% Et$_3$N in methylene chloride, 2 CV's) which was neutralized prior to use on the ISCO. Product was loaded using a wet load using hexanes, eluted using hexanes—10% EtOAc in hexanes, and flushed with EtOAc. The only material to elute (during 10% EtOAc in hexanes elution) was collected and concentrated. NMR had shown no product, only mixtures of materials consistent with decomposition. Product is unstable to isolation using methods such as distillation, silica gel chromatography, as well as neutral or basic alumina chromatography.

Comparative Example 5

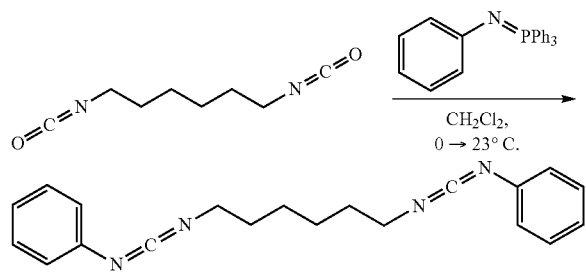

A solution of N-(Triphenylphosphoranylidene)aniline (297.0 mg, 0.84 mmol, 2.00 eq) in CH$_2$Cl$_2$ (5.0 mL) under nitrogen was placed in an ice water bath for 20 minutes upon which hexamethylene diisocyanate (70.6 mg, 67.5 ul, 0.42 mmol, 1.00 eq) was added neat via syringe. The clear colorless solution was allowed to stir (500 rpm) for 14 hrs at 23° C. The clear colorless solution was diluted with hexanes (10 mL) and the resultant white mixture was concentrated to ~1 mL via rotary evaporation, further diluted with hexanes (10 mL), suction filtered, and concentrated. NMR of the crude gum had shown desired product along with mono-carbodiimide/monoisocyanate adduct and TPPO. Attempts to purify the crude mixture via distillation using a Kuglerohr short path apparatus in vacuo failed due to complete degradation of the product during the distillation process. No product distilled and NMR had shown only decomposed material in the initial distill pot. Product is unstable to isolation using methods such as distillation, silica gel chromatography, as well as neutral or basic alumina chromatography.

Comparative Example 6

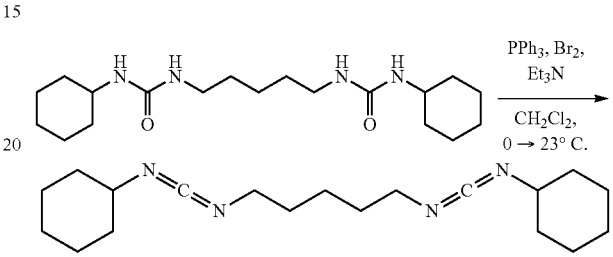

A solution of PPh$_3$ (74.0 mg, 0.28 mmol, 2.50 eq) in CH$_2$Cl$_2$ (2.0 mL) under nitrogen was placed in an ice water bath and stirred (500 rpm) for 15 mins upon which bromine (22.6 mg, 7.4 ul, 0.28 mmol, 2.50 eq) was added neat via syringe. After 15 mins Et$_3$N (57.6 mg, 80.0 ul, 0.57 mmol, 5.00 eq) was added via syringe. After an additional 15 mins the solid urea (40.0 mg, 0.11 mmol, 1.00 eq) was added all at once. After stirring for 24 hrs gradually warming to 23° C. in the process, the golden yellow reaction mixture was diluted with hexanes (10 mL), stirred for 10 mins, suction filtered and concentrated. NMR of the filtrate solution had shown no product and NMR of the filtered solid had shown trace mono-urea mono-carbodiimde, triethylammonium hydrochloride, triphenylphosphine oxide, and several other impurities of polymerization, but no desired product was observed nor SM remaining.

Comparative Example 7

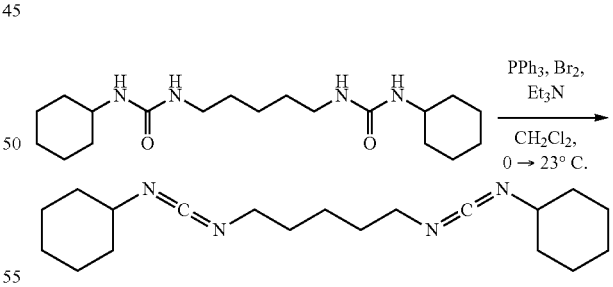

A solution of PPh$_3$ (73.4 mg, 0.28 mmol, 2.50 eq) in CH$_2$Cl$_2$ (5.0 mL) under nitrogen was placed in an ice water bath and stirred (500 rpm) for 15 mins upon which bromine (44.7 mg, 14.0 ul, 0.28 mmol, 2.50 eq) was added neat via syringe. After 15 mins Et$_3$N (57.7 mg, 80.0 ul, 0.57 mmol, 5.00 eq) was added via syringe. After an additional 15 mins the solid urea (40.0 mg, 0.11 mmol, 1.00 eq) was added all at once. After 10 mins the golden yellow mixture was removed from the ice water bath and stirred vigorously (700 rpm) at 23° C. for 36 hrs. The clear golden yellow solution was placed in an ice water bath and diluted with hexanes (20 mL). After 30 mins the white heterogeneous mixture was suction filtered over a pad of diatomaceous silica using cold hexanes and concentrated. NMR of the filtrate solution had shown product with Triphenylphosphine oxide. The white mixture was diluted with hexanes (10 mL) and placed in a bath cooled to −78° C. After 1 hr the mixture was suction filtered over a pad of diatomaceous silica using hexanes chilled in a bath cooled to −78° C. NMR of the filtrate mixture had shown product with some TPPO remaining. Product is unstable to silica gel, basic alumina, or neutral alumina. Product is unstable to isolation using methods such as distillation, silica gel chromatography, as well as neutral or basic alumina chromatography.

Comparative Example 8

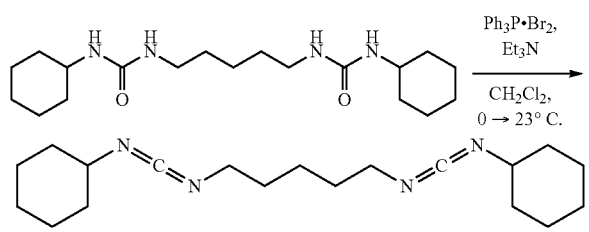

A solution of triphenylphosphine dibromide (116.1 mg, 0.28 mmol, 2.50 eq) and Et₃N (57.6 mg, 80.0 ul, 0.57 mmol, 5.00 eq) in CH₂Cl₂ (2.0 mL) under nitrogen was placed in a bath cooled to −78° C. and stirred (500 rpm) for 30 mins upon which the solid urea (40.0 mg, 0.11 mmol, 1.00 eq) was added all at once. The white heterogeneous mixture was allowed to warm to 23° C. over 16 hrs upon which hexanes (10 mL) was added to precipitate out triphenylphosphine oxide (TPPO). The mixture was placed in an ice water cooling bath for 30 minutes while stirring vigorously (1000 rpm) upon which it was suction filtered over a pad of diatomaceous silica using cold hexanes and the filtrate solution was concentrated. NMR of the filtrate solution (now a white solid) had shown and a complex mixture of products. Attempts to triturate the material with hexanes at 0° C. as well at −78° C. was not successful as TPPO eluted through the pad of diatomaceous silica during filtration even using chilled hexanes. 2-D TLC had indicated that the material is stable to silica gel so attempts to purify the material via silica gel chromatography were conducted using the ISCO; hexanes—10% EtOAc in hexanes (Rf of product is ~0.75 in 10% EtOAc in hexanes) followed by EtOAc flush however no product was eluted and only material to elute is TPPO. Product is unstable to isolation using methods such as distillation, silica gel chromatography, as well as neutral or basic alumina chromatography.

Comparative Example 9

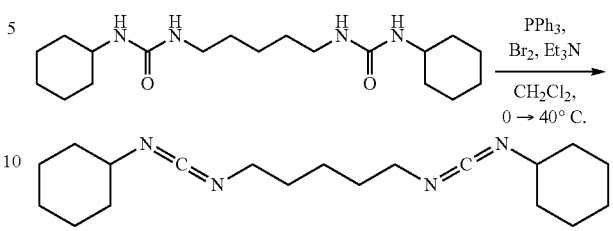

A solution of PPh₃ (73.4 mg, 0.28 mmol, 2.50 eq) in CH₂Cl₂ (5.0 mL) under nitrogen was placed in an ice water bath and stirred (500 rpm) for 15 mins upon which bromine (44.7 mg, 14.0 ul, 0.28 mmol, 2.50 eq) was added neat via syringe. After 15 mins Et₃N (57.7 mg, 80.0 ul, 0.57 mmol, 5.00 eq) was added via syringe. After an additional 15 mins the solid urea (40.0 mg, 0.11 mmol, 1.00 eq) was added all at once. After 10 mins the golden yellow mixture was removed from the ice water bath, placed in a mantle heated to 40° C. and stirred vigorously (700 rpm) at 40° C. for 24 hrs. The golden brown solution was diluted with hexanes (10 mL) and placed in an ice water bath for 30 mins upon which the yellow heterogeneous mixture was suction filtered cold over a pad of diatomaceous silica using cold hexanes and concentrated. NMR of the filtrate solution had shown a complex mixture of products. Product is unstable to isolation using methods such as distillation, silica gel chromatography, as well as neutral or basic alumina chromatography.

Comparative Example 10

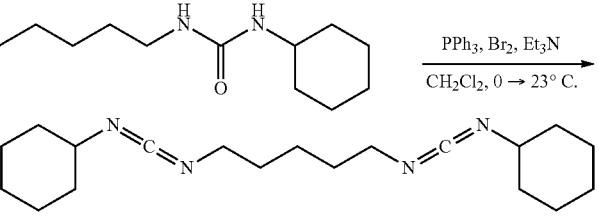

A solution of PPh₃ (440.4 mg, 1.68 mmol, 2.50 eq) in CH₂Cl₂ (30.0 mL) under nitrogen was placed in an ice water bath and stirred (700 rpm) for 15 mins upon which bromine (268.2 mg, 84.0 ul, 1.68 mmol, 2.50 eq) was added neat via syringe. After 15 mins Et₃N (346.2 mg, 480.0 ul, 3.42 mmol, 5.00 eq) was added via syringe. After an additional 15 mins the solid urea (240.0 mg, 0.66 mmol, 1.00 eq) was added all at once. After 10 mins the pale golden yellow mixture was removed from the ice water bath and stirred vigorously (1000 rpm) at 23° C. After 48 hrs the pale yellow solution was concentrated to ~5 mL via rotary evaporation (no water bath), diluted with hexanes (35 mL), cooled in an ice water bath for 30 mins, and the resultant white mixture was suction filtered over diatomaceous silica using cold hexanes. The mixture was fully concentrated in vacuo, diluted with 20 mL of pentane, and the white mixture was placed in a bath cooled to −78° C. for 30 mins, and suction filtered over a pad of diatomaceous silica using cold pentane which was chilled in a bath cooled to −78° C. for 30 mins. The clear colorless solution was fully concentrated to reveal the biscarbodiimide as a clear colorless oil (186.8 mg, 0.59 mmol, 89%, ~95% pure). Residual moisture in the biscarbodiimide was then azeotropically removed using toluene (4×3 mL) in vacuo. NMR of the clear colorless oil had shown product of ~95% purity with triphenyl phosphine oxide remaining and toluene. Separation techniques were unsuccessful in removing the impurities.

$^1$H NMR (400 MHz, Chloroform-d) δ 3.19 (t, J=6.8 Hz, 6H), 1.99-1.81 (m, 4H), 1.72 (ddd, J=13.1, 5.4, 2.8 Hz, 4H), 1.65-1.50 (m, 6H), 1.50-1.38 (m, 2H), 1.38-1.09 (m, 10H).

$^{13}$C NMR (126 MHz, Chloroform-d) δ 140.02, 55.64, 46.69, 34.86, 30.93, 25.43, 24.57, 24.15.

Comparative Example 11

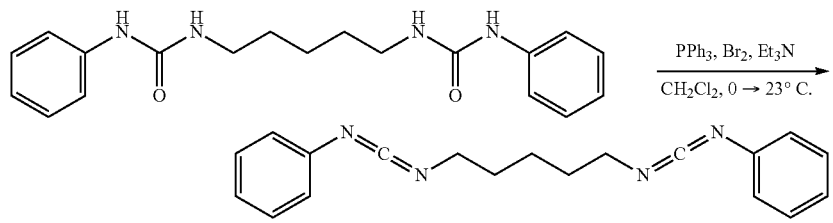

A solution of PPh$_3$ (2.007 g, 7.65 mmol, 2.50 eq) in CH$_2$Cl$_2$ (130.0 mL) under nitrogen was placed in an ice water bath and stirred vigorously (700 rpm) for 30 mins upon which bromine (1.223 g, 394.0 ul, 7.65 mmol, 2.50 eq) was added neat via syringe. After 30 mins Et$_3$N (1.548 g, 2.10 ml, 15.30 mmol, 5.00 eq) was added via syringe. After an additional 15 mins the solid urea (1.043 g, 3.06 mmol, 1.00 eq) was added all at once. After 10 mins the pale golden yellow mixture was removed from the ice water bath and stirred vigorously (1000 rpm) at 23° C. After 48 hrs the pale yellow solution was concentrated to ~5 mL via rotary evaporation (no water bath), diluted with hexanes (150 mL), cooled in an ice water bath for 30 mins, and the resultant white mixture was suction filtered over diatomaceous silica using cold hexanes. The mixture was fully concentrated in vacuo, diluted with 20 mL of pentane, and the white mixture was placed in a bath cooled to −78° C. for 1 hr, suction filtered over a pad of diatomaceous silica using pentane which was also chilled in a bath cooled to −78° C., and fully concentrated to reveal the biscarbodiimide as a clear pale yellow oil (0.131 g, 0.430 mmol, 14%, ~95% pure). $^1$H-, $^{13}$C-, and $^{31}$P-NMR of the clear pale yellow oil had shown product with triphenylphosphine oxide and triphenylphosphine remaining.

$^1$H NMR (400 MHz, Chloroform-d) δ 7.34-7.28 (m, 2H), 7.26-7.23 (m, 2H), 7.11-7.03 (m, 7H), 3.42 (t, J=6.7 Hz, 5H), 1.78-1.64 (m, 5H), 1.61-1.47 (m, 3H).

$^{13}$C NMR (100 MHz, Chloroform-d) δ 140.06, 129.34, 124.64, 123.48, 46.61, 30.80, 24.07.

Comparative Example 12

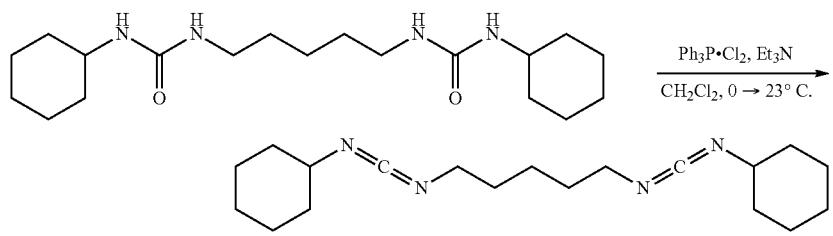

A slurry of triphenylphosphorane dichloride (189.0 mg, 0.5672 mmol, 2.00 eq) and Et$_3$N (0.077 g, 0.10 mL, 0.709 mmol, 2.50 eq) in CH$_2$Cl$_2$ (10 mL) in a nitrogen filled glovebox was removed from the glovebox, placed under nitrogen immediately, placed in an ice water bath for 30 mins and then the bisurea (0.100 g, 0.2836 mmol, 1.00 eq) was added as a solid. After stirring for 24 hrs hexanes (20 mL) was added to precipitate out triphenylphosphine oxide (TPPO). The mixture was placed in an ice water cooling bath for 30 minutes while stirring vigorously (1000 rpm) upon which it was suction filtered over a pad of diatomaceous silica using cold hexanes and the filtrate solution was concentrated. NMR of the filtrate solution (now a white solid) had shown a complex mixture of products due to decomposition and material consistent of incomplete conversion of SM. Attempts to triturate the material with hexanes at 0° C. as well at −78° C. was not successful as they eluted through the pad of diatomaceous silica during filtration using chilled hexanes or pentane. Product is unstable to isolation using methods such as distillation, silica gel chromatography, as well as neutral or basic alumina chromatography.

Comparative Example 13

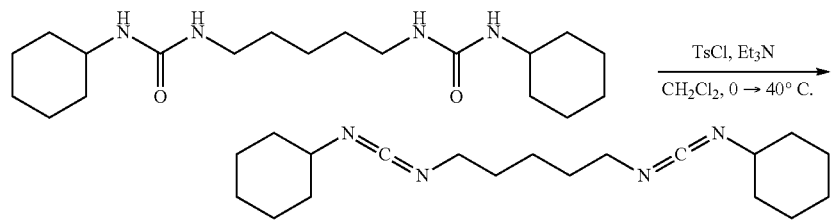

A solution of the bisurea (0.100 g, 0.2836 mmol, 1.00 eq) and Et$_3$N (0.143 g, 0.20 mL, 1.418 mmol, 5.00 eq) in anhydrous CH$_2$Cl$_2$ (10 mL) under nitrogen was placed in an ice water bath for 30 mins upon which solid p-TsCl (0.136 g, 0.7090 mmol, 2.50 eq) was added all at once. After the complete addition the pale yellow heterogeneous mixture was removed from the ice bath, stirred (400 rpm) for 30 mins at 23° C. and then placed in a mantle heated to 40° C. After 2 hrs the orange-brown heterogeneous mixture was removed from the mantle, allowed to cool to 23° C., diluted with hexanes (50 mL), placed in an ice water bath for 30 mins, suction filtered cold, and concentrated. NMR of the filtrate had shown no product or starting bisurea, only a complex mixture of products consistent with decomposition. NMR of the filtered solid had shown the same along with Et$_3$NHCl.

Comparative Example 14

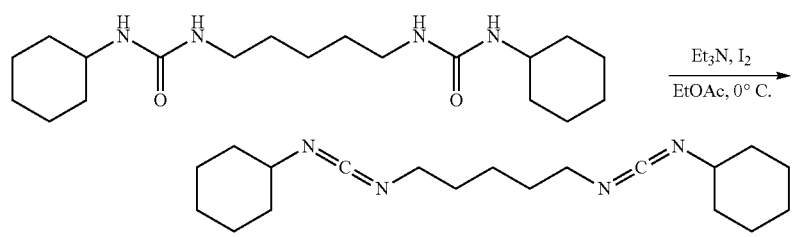

A suspension of the bisthiourea (0.100 g, 0.2600 mmol, 1.00 eq) and Et₃N (0.115 g, 0.16 mL, 1.144 mmol, 4.40 eq) in EtOAc (3 mL) under nitrogen was placed in an ice water bath for 30 mins upon which solid I₂ (0.290 g, 1.144 mmol, 4.40 eq) was added slowly over 30 mins in 6 separate portions. After the complete addition the pale yellow heterogeneous mixture was stirred (500 rpm) for 30 mins, diluted with hexanes (30 mL), placed in an ice water bath for 30 mins, suction filtered cold through a pad of diatomaceous silica, and concentrated. NMR of the filtrate had shown product and a complex mixture of products consistent with decomposition. Attempts to purify the mixture using cold (−78° C.) trituration with pentane failed to provide pure product. Product is unstable to isolation using methods such as distillation, silica gel chromatography, as well as neutral or basic alumina chromatography.

Comparative Example 15

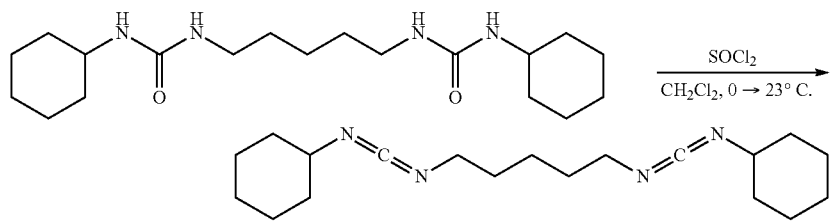

A solution of the bisurea (0.100 g, 0.2836 mmol, 1.00 eq) in CH₂Cl₂ (5 mL) under nitrogen was placed in an ice water bath for 30 mins upon which neat SOCl₂ (68.1 mg, 42.0 μL, 0.5720 mmol, 2.02 eq) was added via syringe. After the complete addition the pale yellow heterogeneous mixture was stirred (500 rpm) for 30 mins, removed from the ice bath, allowed to stir at 23° C. for 2 hrs, diluted with hexanes (30 mL), placed in an ice water bath for 30 mins, suction filtered cold through a pad of diatomaceous silica, and concentrated. NMR of the filtrate had shown a complex mixture of products consistent with decomposition and polymerization.

Comparative Example 16

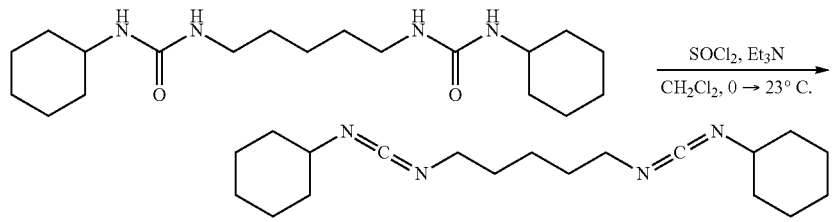

A solution of the bisurea (0.100 g, 0.2836 mmol, 1.00 eq) and Et₃N (0.143 g, 0.20 mL, 1.418 mmol, 5.00 eq) in CH₂Cl₂ (10 mL) under nitrogen was placed in an ice water bath for 30 mins upon which neat SOCl₂ (68.1 mg, 42.0 μL, 0.5720 mmol, 2.02 eq) was added via syringe. After the complete addition the pale yellow heterogeneous mixture was stirred (500 rpm) for 30 mins, removed from the ice bath, allowed to stir at 23° C. for 2 hrs, diluted with hexanes (30 mL), placed in an ice water bath for 30 mins, suction filtered cold through a pad of diatomaceous silica, and concentrated. NMR of the filtrate had shown a complex mixture of products consistent with decomposition and polymerization.

Comparative Example 17

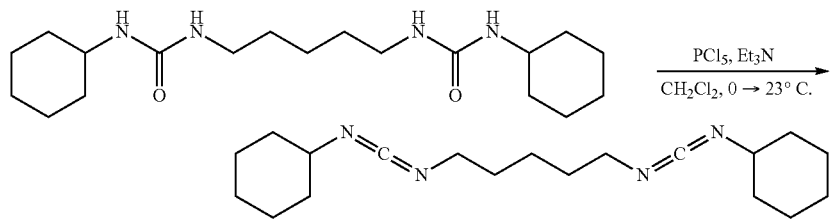

A solution of the bisurea (0.100 g, 0.2836 mmol, 1.00 eq) and $Et_3N$ (0.143 g, 0.20 mL, 1.418 mmol, 5.00 eq) in $CH_2Cl_2$ (10 mL) under nitrogen was placed in an ice water bath for 30 mins upon which solid $PCl_5$ (118.0 mg, 0.5720 mmol, 2.02 eq) was added all at once. After the complete addition the pale yellow heterogeneous mixture was stirred (500 rpm) for 30 mins, removed from the ice bath, allowed to stir at 23° C. for 2 hrs, diluted with hexanes (30 mL), placed in an ice water bath for 30 mins, suction filtered cold through a pad of diatomaceous silica, and concentrated. NMR of the filtrate had shown a complex mixture of products consistent with decomposition and polymerization.

Comparative Example 18

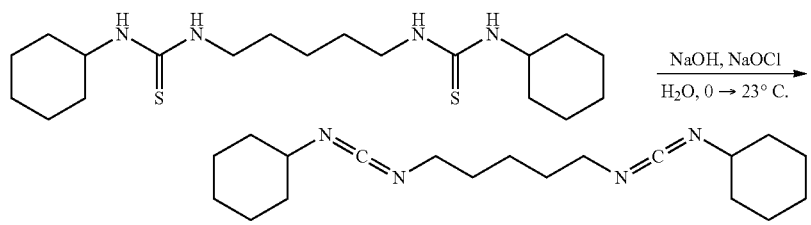

A suspension of the bisthiourea (0.100 g, 0.2600 mmol, 1.00 eq) in $H_2O$ (5 mL) under nitrogen was placed in an ice water bath for 30 mins upon which an aqueous solution of NaOH (0.52 mL, 0.5200 mmol, 2.00 eq, 1 N) and NaOCl (77.4 mg, 2.6 mL, 1.040 mmol, 4.00 eq, 3% w/w) was added in a slow dropwise manner sequentially. After the complete addition the pale yellow heterogeneous mixture was stirred (500 rpm) for 30 mins, removed from the ice water bath, allowed to stir for 4 hrs at 23° C., diluted with hexanes (30 mL), placed in an ice water bath for 30 mins, suction filtered cold through a pad of diatomaceous silica, poured into a separatory funnel, partitioned, residual organics were extracted from the aqueous layer using hexanes (2×10 mL), combined, washed with brine (1×10 mL), dried over solid $Na_2SO_4$, decanted, and concentrated. NMR of the filtrate had shown minimal product and a complex mixture of products consistent with decomposition and polymerization. Attempts to purify the mixture using cold (−78° C.) trituration with pentane failed to provide any pure product.

Comparative Example 19

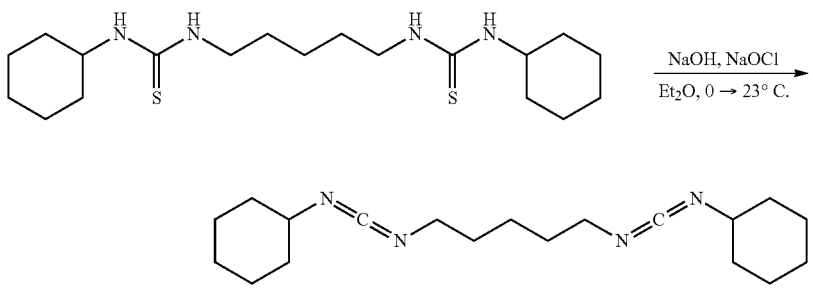

A suspension of the bisthiourea (0.100 g, 0.2600 mmol, 1.00 eq) in Et$_2$O (5 mL) under nitrogen was placed in an ice water bath for 30 mins upon which an aqueous solution of NaOH (0.52 mL, 0.5200 mmol, 2.00 eq, 1 N) and NaOCl (77.4 mg, 2.6 mL, 1.040 mmol, 4.00 eq, 3% w/w) was added in a slow dropwise manner. After the complete addition the pale yellow heterogeneous mixture was stirred (500 rpm) for 30 mins, removed from the ice water bath, allowed to stir for 4 hrs at 23° C., diluted with hexanes (30 mL), placed in an ice water bath for 30 mins, suction filtered cold through a pad of diatomaceous silica, poured into a separatory funnel, partitioned, residual organics were extracted from the aqueous layer using hexanes (2×10 mL), combined, washed with brine (1×10 mL), dried over solid Na$_2$SO$_4$, decanted, and concentrated. NMR of the filtrate had shown minimal product and a complex mixture of products consistent with decomposition and polymerization. Attempts to purify the mixture using cold (−78° C.) trituration with pentane failed to provide any pure product.

The following examples illustrate the synthesis and purification of biscarbodiimides.

Example 1

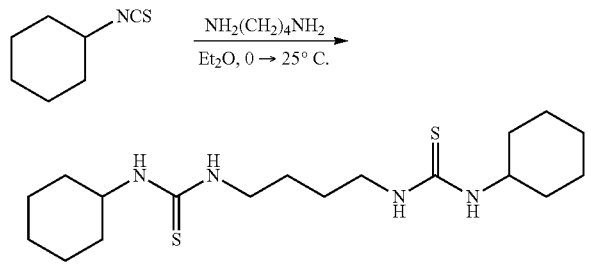

A vigorously stirring (700 rpm) solution of cyclohexylisothiocyanate (2.000 g, 2.0 mL, 14.161 mmol, 2.00 eq) in ether (50 mL) was placed in an ice water bath for 20 mins upon which 1,4-diaminobutane (0.624 g, 0.71 mL, 7.081 mmol, 1.00 eq) was added neat via syringe. The now white heterogeneous mixture was allowed to stir vigorously for 12 hrs warming gradually to 23° C. The white heterogeneous mixture was then placed in an ice water bath for 1 hr, suction filtered cold, washed with cold diethyl ether (3×20 mL), the white powder was collected, and dried in vacuo to afford the bisthiourea (2.064 g, 4.598 mmol, 76%). NMR had shown pure product:

$^1$H NMR (500 MHz, DMSO-d$_6$) δ 7.23 (s, 2H), 7.17 (s, 2H), 3.91 (s, 2H), 3.46-3.23 (m, 4H), 1.88-1.71 (m, 4H), 1.63 (dt, J=13.0, 3.9 Hz, 4H), 1.52 (dt, J=12.8, 3.9 Hz, 2H), 1.49-1.29 (m, 4H), 1.24 (qt, J=12.4, 3.3 Hz, 4H), 1.18-1.00 (m, 6H).

$^{13}$C NMR (126 MHz, DMSO-d$_6$) δ 181.50, 43.59, 40.48, 32.76, 26.87, 25.64, 25.00.

This product is used in the following reaction.

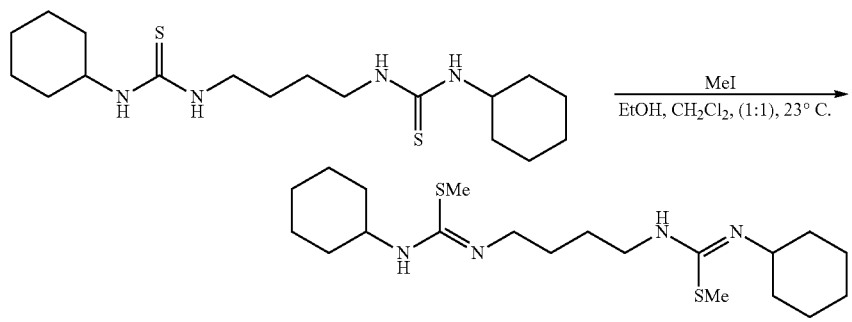

To a white heterogeneous mixture of the bisthiourea (1.0373 g, 2.799 mmol, 1.00 eq) in EtOH and CH$_2$Cl$_2$ (40 mL, 1:1) was added MeI (1.589 g, 0.70 mL, 11.20 mmol, 4.00 eq). The mixture was allowed to stir (500 rpm) at 23° C. for 12 hrs upon which the clear pale yellow solution was diluted with a saturated aqueous mixture of NaHCO$_3$ (50 mL), then aqueous NaOH (10 mL, 1 N), the biphasic mixture was stirred vigorously (1000 rpm) for 5 mins, poured into a separatory funnel, paritioned, the organic layer was washed with an aqueous mixture of NaHCO$_3$ (3×25 mL), residual organics were back extracted from the aqueous layer using CH$_2$Cl$_2$ (2×25 mL), combined, washed with brine (2×20 mL), dried over solid Na$_2$SO$_4$, decanted, and concentrated. NMR had shown product along minor impurities, however signals are broad due to the presence of multiple tautomers:

$^1$H NMR (500 MHz, Chloroform-d) δ 4.18 (d, J=82.0 Hz, 2H), 3.45 (d, J=38.8 Hz, 2H), 3.26 (s, 4H), 2.35 (s, 6H), 1.85 (s, 4H), 1.70 (dq, J=13.1, 3.9 Hz, 4H), 1.66-1.51 (m, 6H), 1.41-1.24 (m, 6H), 1.18 (dq, J=15.7, 11.8 Hz, 6H).

$^{13}$C NMR (126 MHz, Chloroform-d) δ 157.96-157.83 (m), 33.98, 28.42, 25.75, 24.96, 22.51, 14.40, 14.32.

The product is used in the following reaction crude without further purification.

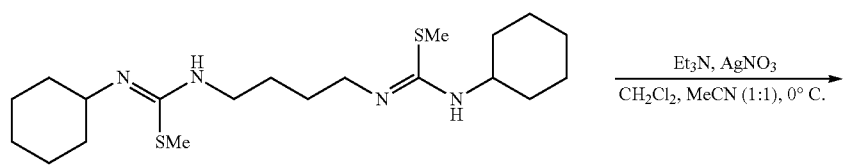

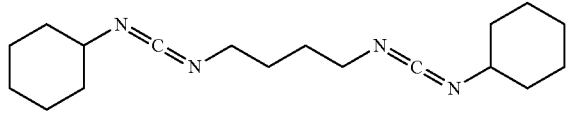

A solution of the crude isothiourea (1.0785 g, 2.705 mmol, 1.00 eq) and Et$_3$N (0.575 g, 0.79 mL, 5.681 mmol, 2.10 eq) in acetonitrile-CH$_2$Cl$_2$ (27.0 mL, 1:1) in an oven-dried brown jar protected from light was placed in an ice water cooling bath and stirred (300 rpm) for 30 mins upon which solid AgNO$_3$ (0.942 g, 5.545 mmol, 2.05 eq) was added all at once. After 2 hrs the yellow heterogeneous mixture was diluted with hexanes (20 mL), stirred vigorously (1000 rpm) for 5 mins, suction filtered cold over a pad of diatomaceous silica with hexanes, and concentrated to ~5 mL. The mixture was diluted with hexanes (20 mL), and concentrated to ~5 mL. This process was repeated twice more, and then the hexanes mixture was suction filtered over a pad of diatomaceous silica using hexanes and concentrated in vacuo to afford the biscarbodiimide (0.544 g, 1.799 mmol, 66%) as a clear colorless oil. NMR had shown pure product:

$^1$H NMR (500 MHz, Chloroform-d) δ 3.26-3.13 (m, 6H), 1.92-1.82 (m, 4H), 1.76-1.67 (m, 4H), 1.67-1.57 (m, 4H), 1.57-1.49 (m, 2H), 1.36-1.12 (m, 10H).

$^{13}$C NMR (126 MHz, Chloroform-d) δ 139.87, 55.61, 46.39, 34.83, 28.64, 25.40, 24.54.

Example 2

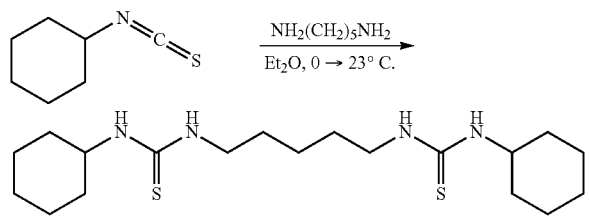

A vigorously stirring (700 rpm) clear colorless solution of cyclohexylisothiocyanate (2.000 g, 2.01 mL, 14.16 mol, 2.00 eq) in diethyl ether (25.0 mL) under nitrogen was placed in an ice water bath for 20 mins upon which cadaverine (0.724 g, 0.83 mL, 7.08 mmol, 1.00 eq) was added neat via syringe. The now white heterogeneous mixture was allowed to stir vigorously for 12 hrs while gradually warming to 23° C. The white mixture was then placed in an ice water bath for 1 hr, suction filtered cold, the white filter cake was washed with cold ethyl ether (3×20 mL), and the resultant white paste was dried in vacuo to afford the bisthiourea product as free flowing white powder (2.277 g, 5.920 mmol, 84%). $^1$H-NMR had shown product with trace ethyl ether and impurities.

$^1$H NMR (500 MHz, DMSO-d$_6$) δ 7.20 (br s, 2H), 7.14 (br d, J=8.0 Hz, 2H), 3.91 (m, 2H), 3.32 (m, 4H), 1.80 (dt, J=12.2, 4.0 Hz, 4H), 1.63 (dq, J=13.0, 3.9 Hz, 4H), 1.52 (dt, J=12.7, 3.9 Hz, 2H), 1.44 (p, J=7.4 Hz, 4H), 1.30-1.18 (m, 6H), 1.18-1.05 (m, 6H).

$^{13}$C NMR (126 MHz, DMSO-d$_6$) δ 181.39, 52.04, 43.78, 32.77, 29.06, 25.65, 24.99, 24.33.

The product is used in the following reaction without purification.

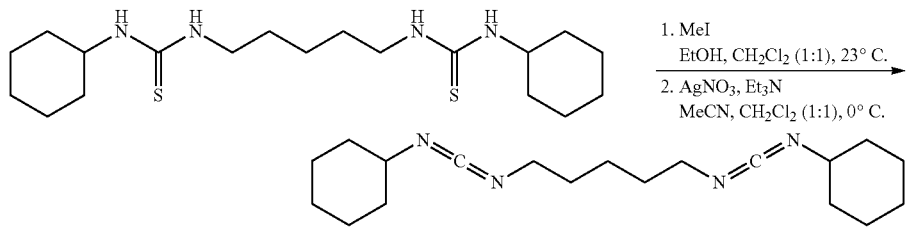

To a white heterogeneous mixture of the bisthiourea (1.862 g, 4.841 mmol, 1.00 eq) in ethanol and CH$_2$Cl$_2$ (40 mL, 1:1) was added iodomethane (2.95 g, 1.29 mL, 20.80 mmol, 4.30 eq). The mixture changed to a clear pale yellow solution after 10 mins which was then allowed to stir (300 rpm) for 12 hrs at 23° C. The clear colorless solution was then neutralized with an aqueous saturated mixture of NaHCO$_3$ (60 mL), diluted with CH$_2$Cl$_2$ (20 mL), stirred vigorously (1000 rpm) for 2 mins, an aqueous solution of NaOH (10 mL, 1 N) was added, the biphasic mixture was poured into a separatory funnel, partitioned, and the organic layer was washed with an aqueous saturated mixture of NaHCO$_3$ (3×20 mL). Residual organics were back extracted from the aqueous layer using CH$_2$Cl$_2$ (3×10 mL), combined, washed with brine (1×20 mL), dried over solid Na$_2$SO$_4$, suction filtered over a pad of solid Na$_2$SO$_4$, and concentrated. NMR had shown product along with minor impurities and residual solvent so the crude material was further dried in vacuo to afford the bisisothiourea as a golden yellow viscous oil (1.945 g, 4.713 mmol, 97%). The product was used in the subsequent reaction without further purification.

A solution of the bismethyl isothiourea (1.000 g, 2.423 mmol, 1.00 eq) and Et$_3$N (0.515 g, 0.71 mL, 5.088 mmol, 2.10 eq) in acetonitrile-CH$_2$Cl$_2$ (25.0 mL, 1:1) in an oven-dried brown vial protected from light was placed in an ice water cooling bath and stirred (300 rpm) for 30 mins upon which solid AgNO$_3$ (0.844 g, 4.967 mmol, 2.05 eq) was added all at once. After 1 hr the yellow heterogeneous mixture was diluted with hexanes (20 mL), stirred vigorously (1000 rpm) for 5 mins, suction filtered cold over a pad of diatomaceous silica with hexanes, and concentrated to ~5 mL. The mixture was diluted with hexanes (20 mL), and concentrated to ~5 mL. This process was repeated twice more, and then the hexanes mixture was suction filtered over a pad of diatomaceous silica using hexanes and concentrated in vacuo to afford the biscarbodiimide (0.520 g, 1.643 mmol, 68%) as a clear colorless oil. NMR indicates pure biscarbodiimide:

¹H NMR (500 MHz, Chloroform-d) δ 3.21 (t, J=6.8 Hz, 6H), 1.94-1.84 (m, 5H), 1.80-1.69 (m, 5H), 1.64-1.52 (m, 7H), 1.48-1.40 (m, 2H), 1.37-1.15 (m, 10H).

¹³C NMR (126 MHz, Chloroform-d) δ 140.01, 55.64, 46.68, 34.85, 30.92, 25.42, 24.56, 24.14.

NMR characterization of the crude bisisothiourea:

¹H NMR (500 MHz, Chloroform-d) δ 3.25 (s, 4H), 2.35 (s, 6H), 1.88 (s, 2H), 1.71 (d, J=13.3 Hz, 4H), 1.66-1.54 (m, 8H), 1.47-1.29 (m, 6H), 1.29-1.12 (m, 6H).

Example 3

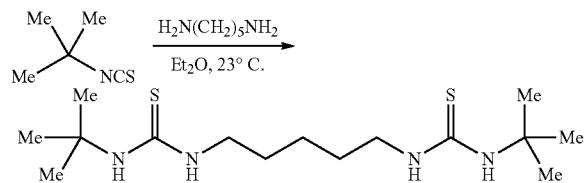

To a vigorously stirring (1000 rpm) solution of the thioisocyanate (2.000 g, 2.20 mL, 17.36 mmol, 2.00 eq) in anhydrous ethyl ether (20 mL) at 23° C. under nitrogen was added a solution of cadaverine (0.887 g, 1.02 mL, 8.68 mmol, 1.00 eq) in anhydrous ethyl ether (10 mL). The clear colorless solution is rapidly stirred for 12 hrs at 23° C. becoming a white heterogeneous mixture in the process. NMR of an aliquot of the reaction indicated the completion of the reaction and the ether was removed in vacuo to afford the bisthiourea as a white solid (2.880 g, 17.31 mmol, 100%). NMR indicates pure product:

¹H NMR (500 MHz, Chloroform-d) δ 6.23-6.05 (m, 2H), 5.93 (s, 2H), 3.54 (q, J=7.1 Hz, 4H), 1.64 (p, J=7.3 Hz, 5H), 1.42 (s, 18H), 1.41-1.36 (m, 2H).

¹³C NMR (126 MHz, Chloroform-d) δ 181.02, 52.95, 44.91, 29.54, 28.61, 23.92.

The product is used in the following reaction.

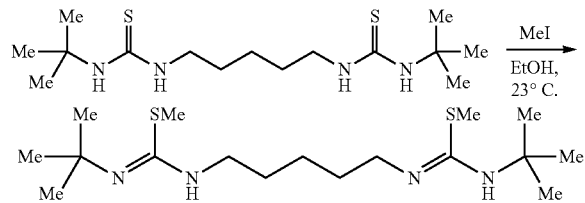

To a solution of the bisthiourea (800.0 mg, 2.40 mmol, 1.00 eq) in ethanol (6.0 mL) at 23° C. was added iodomethane (1.36 g, 0.60 mL, 9.60 mmol, 4.00 eq). The clear colorless solution was stirred vigorously (500 rpm) for 12 hrs. The now white mixture was diluted with a saturated aqueous mixture of NaHCO₃ (50 mL) and diluted with ethyl ether (30 mL). The slightly opaque mixture was stirred vigorously (1000 rpm) for 2 mins upon which an aqueous solution of NaOH (5 mL, 1 N) was added. The now clear colorless biphasic mixture was poured into a separatory funnel, partitioned, and the organics were washed with a saturated aqueous mixture of NaHCO₃ (3×20 mL). Residual organics were back extracted from the aqueous with ethyl ether (3×10 mL), dried over solid Na₂SO₄, decanted, and concentrated to reveal a pale golden brown oil (822.0 mg, 2.28 mol, 95%). NMR of the oil indicates pure product:

¹H NMR (500 MHz, Chloroform-d) δ 3.77 (s, 2H), 3.32 (t, J=6.8 Hz, 4H), 2.31 (s, 6H), 1.57 (p, J=7.1 Hz, 4H), 1.44 (td, J=7.7, 4.7 Hz, 2H), 1.34 (s, 18H).

¹³C NMR (126 MHz, Chloroform-d) δ 146.44, 52.28, 51.52, 31.91, 28.88, 25.59, 15.36.

The product is used in the following reaction without purification.

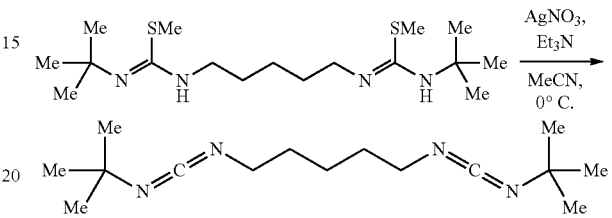

A solution of the crude bismethylisothiourea (2.701 g, 7.499 mmol, 1.00 eq) and Et₃N (1.594 g, 2.20 mL, 15.748 mmol, 2.10 eq) in MeCN (75 mL) was placed in an ice water bath for 30 mins upon which solid AgNO₃ (2.611 g, 15.373 mmol, 2.05 eq) was added all at once. After stirring vigorously (500 rpm) for 2 hrs hexanes (100 mL) was added, the yellow biphasic heterogeneous mixture was suction filtered over diatomaceous silica, concentrated to ~10 mL, hexanes (50 mL) was added, the mixture was concentrated to ~10 mL, this was repeated 3× more, the resultant yellow heterogeneous mixture was then diluted with hexanes (50 mL), suction filtered over a pad of diatomaceous silica, and concentrated to afford the biscarbodiimide as a clear colorless oil (1.698 g, 6.422 mmol, 86%). NMR indicates pure product:

¹H NMR (500 MHz, Chloroform-d) δ 3.21 (t, J=6.9 Hz, 4H), 1.63-1.54 (m, 4H), 1.50-1.41 (m, 2H), 1.27 (s, 18H).

¹³C NMR (101 MHz, Chloroform-d) δ 139.90, 55.03, 46.76, 31.32, 31.00, 24.18.

Example 4

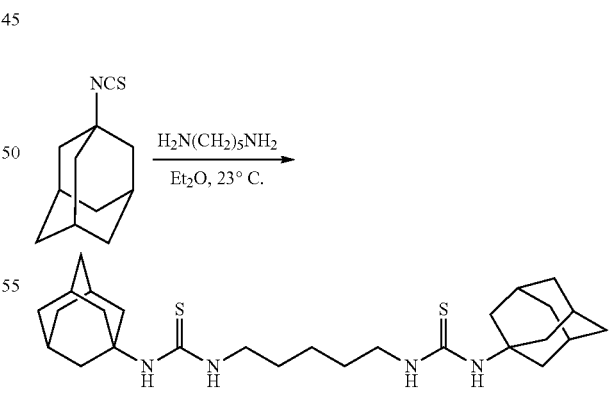

A solution of adamantyl isothiocyanate (2.00 g, 10.35 mmol, 2.00 eq) in ether (55 mL) at 23° C. was stirred vigorously (700 rpm) upon which cadaverine (0.529 g, 0.61 mL, 5.18 mmol, 1.00 eq) was slowly added neat via syringe. After 12 hrs an NMR of a crude aliquot had shown product along with other impurities. The now white mixture was placed in an ice water cooling bath for 30 mins and suction filtered cold using cold ether. The resulting white solid was washed with cold ether (3×20 mL) and then dried in vacuo to afford the bisthiourea as a white powder (1.901 g, 3.89 mmol, 76%). NMR of the white powder had shown pure product with trace diethyl ether remaining (mixture of tautomers: (*) denotes minor tautomer):

$^1$H NMR (400 MHz, DMSO-d$_6$) δ 7.15 (t, J=5.2 Hz, 2H), 6.82 (s, 2H), 3.27 (q, J=6.1 Hz, 4H), 2.09 (d, J=2.9 Hz, 12H), 2.06-1.91 (m, 6H), 1.58 (d, J=3.1 Hz, 12H), 1.39 (h, J=7.5 Hz, 4H), 1.34-1.16 (m, 2H).

$^{13}$C NMR (126 MHz, DMSO-d$_6$) δ 181.02, 52.98, (43.41*) 43.30, (42.05*) 41.69, 36.44 (33.52*), 29.48, (29.09*) 28.97, 24.45 (24.38*).

The product is used in the following reaction.

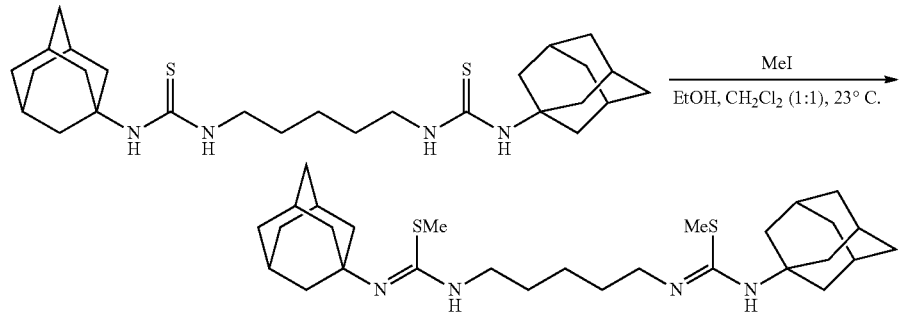

To a solution of the bisthiourea (633.0 mg, 1.30 mmol, 1.00 eq) in ethanol and CH$_2$Cl$_2$ (30.0 mL, 1:1) at 23° C. was added iodomethane (738.0 mg, 0.33 mL, 5.20 mmol, 4.00 eq). The clear colorless solution was stirred (300 rpm) for 12 hrs upon which it was neutralized with an aqueous saturated mixture of NaHCO$_3$ (60 mL) and further diluted with CH$_2$Cl$_2$ (20 mL). The white mixture was stirred vigorously (1000 rpm) for 2 mins and then an aqueous solution of NaOH (15 mL, 1 N) was added. After stirring for 2 mins, the now clear colorless biphasic mixture was poured into a separatory funnel, partitioned, and the organics were washed with an aqueous saturated mixture of NaHCO$_3$ (3×20 mL). Residual organics were back extracted from the aqueous with CH$_2$Cl$_2$ (3×10 mL), combined, washed with brine (20 mL), dried over solid Na$_2$SO$_4$, decanted, and concentrated to afford the bisisothiourea as an off-white solid (660.9 mg, 1.28 mmol, 99%). NMR of the solid indicates product:

$^1$H NMR (400 MHz, Chloroform-d) δ 3.70 (s, 2H), 3.29 (t, J=7.0 Hz, 4H), 2.30 (s, 6H), 2.03 (s, 6H), 1.99 (d, J=2.5 Hz, 12H), 1.64 (d, J=3.1 Hz, 12H), 1.55 (t, J=7.3 Hz, 4H), 1.48-1.37 (m, 2H).

$^{13}$C NMR (126 MHz, Chloroform-d) δ 146.13, 52.90, 51.54, 41.97, 36.63, 31.78, 29.70, 25.51, 24.73, 15.48.

The product is used in the following reaction without further purification.

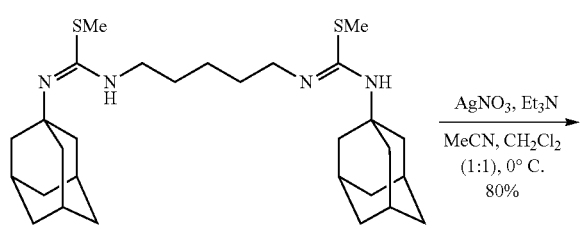

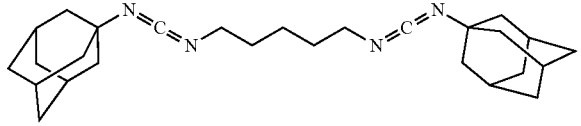

A solution of the bismethyl isothiourea (392.0 mg, 0.7585 mmol, 1.00 eq) and Et$_3$N (160.7 mg, 222.0 ul, 1.594 mmol, 2.10 eq) in acetonitrile-CH$_2$Cl$_2$ (32.0 mL, 1:1) in an oven-dried brown jar protected from light was placed in an ice water cooling bath and stirred (300 rpm) for 30 mins upon which solid AgNO$_3$ (265.0 mg, 1.554 mmol, 2.05 eq) was added all at once. After 1 hr the yellow heterogeneous mixture was diluted with hexanes (20 mL), stirred vigorously (1000 rpm) for 5 mins, suction filtered cold over a pad of diatomaceous silica with hexanes, and concentrated to ~5 mL. The mixture was diluted with hexanes (20 mL), and concentrated to ~5 mL. This process was repeated twice more, and then the hexanes mixture was diluted with hexanes (20 mL), suction filtered over a pad of diatomaceous silica, and concentrated in vacuo to afford the biscarbodiimide (255.9 mg, 0.6084 mmol, 80%) as a clear colorless viscous oil. NMR indicates pure product:

$^1$H NMR (500 MHz, Chloroform-d) δ 3.21 (t, J=6.8 Hz, 4H), 2.09 (s, 6H), 1.78 (d, J=2.8 Hz, 12H), 1.70-1.55 (m, 16H), 1.46 (tt, J=9.5, 5.8 Hz, 2H).

$^{13}$C NMR (101 MHz, Chloroform-d) δ 140.06, 55.13, 46.83, 44.78, 35.98, 30.95, 29.81.

Example 6

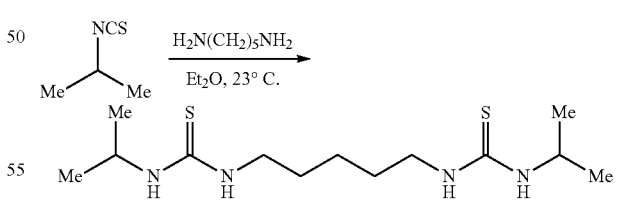

To a vigorously stirring (1000 rpm) solution of the thioisocyanate (2.000 g, 2.11 mL, 19.77 mmol, 2.00 eq) in anhydrous ethyl ether (50 mL) at 23° C. under nitrogen was added a solution of cadaverine (1.010 g, 1.16 mL, 9.88 mmol, 1.00 eq) neat dropwise via syringe over 2 mins. The clear colorless solution instantly changed to a white heterogeneous mixture which was vigorously stirred for 12 hrs. The white mixture was fully concentrated to reveal the bisthiourea (3.01 g, 9.88 mmol, 100%). NMR indicates pure product:

¹H NMR (400 MHz, DMSO-d$_6$) δ 7.16 (s, 2H), 7.09 (d, J=7.9 Hz, 2H), 4.18 (s, 2H), 3.33-3.24 (m, 4H), 1.43 (p, J=7.3 Hz, 4H), 1.21 (tt, J=8.2, 6.0 Hz, 2H), 1.05 (dd, J=6.5, 0.9 Hz, 12H).

¹³C NMR (101 MHz, DMSO-d$_6$) δ 181.25, 45.21, 43.72, 29.03, 24.29, 22.79.

HRMS (ESI): calc'd C$_{13}$H$_{28}$N$_4$S$_2$ [M+1-1]$^+$ as 305.2255; found 305.2285.

The product is used in the following reaction.

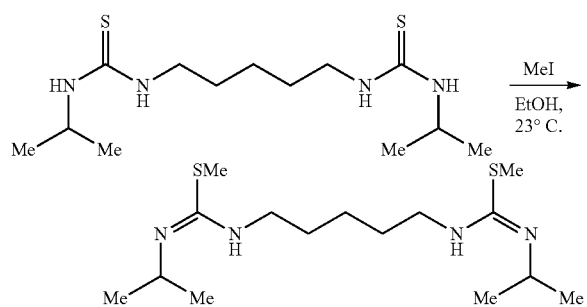

To a mixture of the bisthiourea (850.0 mg, 2.79 mmol, 1.00 eq) in CH$_2$Cl$_2$ and ethanol (40.0 mL, 1:1) at 23° C. was added iodomethane (1.58 g, 0.70 mL, 11.16 mmol, 4.00 eq). The white mixture was stirred (300 rpm) for 12 hrs. The now clear colorless homogeneous solution was neutralized with an aqueous saturated mixture of NaHCO$_3$ (60 mL) and then CH$_2$Cl$_2$ (20 mL) was added. The white biphasic mixture was stirred vigorously (1000 rpm) for 5 mins and then an aqueous solution of NaOH (10 mL, 1 N) was added. The now clear colorless biphasic mixture was poured into a separatory funnel, partitioned, and the organics were washed with an aqueous saturated mixture of NaHCO$_3$ (3×20 mL). Residual organics were back extracted from the aqueous using CH$_2$Cl$_2$ (3×10 mL), combined, washed with brine (20 mL), dried over solid Na$_2$SO$_4$, decanted, and concentrated to afford the isothiourea as an off-white solid (866.7 mg, 2.61 mmol, 94%). NMR of the solid indicates pure product:

¹H NMR (400 MHz, Chloroform-d) δ 3.82 (bs, 3H), 3.23 (bs, 5H), 2.32 (s, 6H), 1.57 (p, J=7.3 Hz, 4H), 1.47-1.34 (m, 2H), 1.11 (d, J=6.3 Hz, 12H).

¹³C NMR (126 MHz, Chloroform-d) δ 149.84, 46.11, 30.63, 24.95, 23.78, 23.59, 14.35.

HRMS (ESI): calc'd C$_{15}$H$_{32}$N$_4$S$_2$ [M+1-1]$^+$ as 333.2630; found 333.2634.

The product is used in the following reaction without purification.

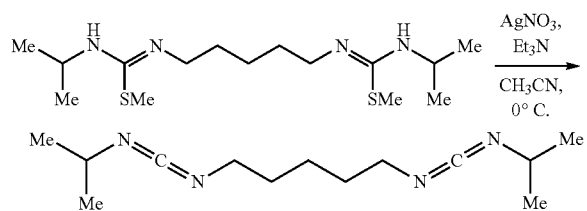

A solution of the bismethylisothiourea (2.363 g, 7.105 mmol, 1.00 eq) and Et$_3$N (1.510 g, 2.10 mL, 14.921 mmol, 2.10 eq) in non-anhydrous acetonitrile (140 mL) in a brown jar protected from light was placed in an ice water bath for 20 mins upon which solid AgNO$_3$ (2.474 g, 14.565 mmol, 2.05 eq) was added all at once. After 2 hrs the yellow heterogeneous mixture was diluted with hexanes (100 mL), stirred vigorously (1000 rpm) for 2 mins, suction filtered cold through a pad of diatomaceous silica, the filtrate was concentrated to ~10 mL, hexanes (50 mL) was added, the mixture was further concentrated to ~10 mL, this process was repeated 3× more, hexanes (50 mL) was added, the heterogeneous mixture was suction filtered through a pad of diatomaceous silica, and concentrated to afford the biscarbodiimide as a clear colorless oil (1.558 g, 6.590 mmol, 93%). NMR indicates pure product:

¹H NMR (500 MHz, Chloroform-d) δ 3.56 (hept, J=6.4 Hz, 2H), 3.22 (t, J=6.8 Hz, 4H), 1.68-1.51 (m, 4H), 1.51-1.37 (m, 2H), 1.22 (d, J=6.4 Hz, 12H).

¹³C NMR (126 MHz, Chloroform-d) δ 140.12, 48.91, 46.65, 30.90, 24.59, 24.11.

HRMS (ESI): calc'd C$_{13}$H$_{24}$N$_4$ [M+H]$^+$ as 237.2035; found 237.2027.

Example 7

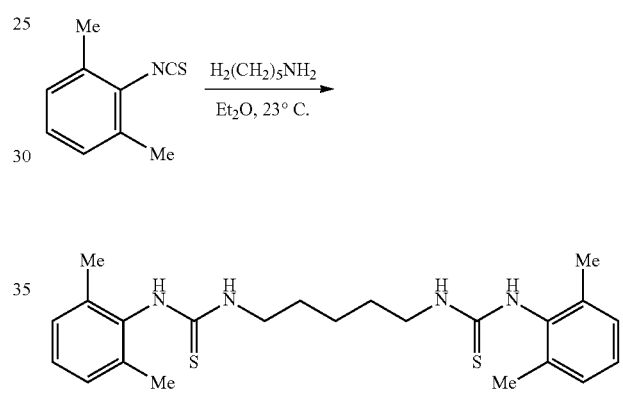

To a vigorously stirring (1000 rpm) solution of 2,6-dimethylphenylisothiocyanate (2.000 g, 1.85 mL, 12.252 mmol, 2.00 eq) in Et$_2$O (65 mL) was added cadaverine (0.626 g, 0.72 mL, 6.126 mmol, 1.00 eq) in slow dropwise fashion over 1 min. The clear colorless solution was allowed to stir vigorously for 12 hrs upon which the white heterogeneous mixture was placed in an ice water bath for 1 hr, suction filtered cold, the white filtered solid was washed with cold Et$_2$O (3×20 mL), and dried in vacuo to afford the bisthiourea as a white powder (2.331 g, 5.438 mmol, 89%). NMR indicates pure product:

¹H NMR (400 MHz, DMSO-d$_6$) δ 7.05 (s, 6H), 3.49-3.20 (m, 4H), 2.09 (s, 12H), 1.45 (s, 4H), 1.20 (s, 2H).

¹H NMR (500 MHz, Acetone-d$_6$) δ 8.33 (s, 1H), 7.11 (d, J=7.4 Hz, 5H), 6.47 (s, 1H), 3.55 (q, J=7.4, 6.7 Hz, 4H), 2.22 (s, 12H), 1.57 (s, 4H), 1.27 (s, 2H).

¹³C NMR (126 MHz, Acetone-d$_6$) δ 181.31, 137.25, 137.22, 128.31, 44.28, 23.82, 17.40.

HRMS (ESI): calc'd C$_{23}$H$_{32}$N$_4$S$_2$ [M+H]$^+$ as 429.2141; found 429.2779.

The product is used in the following reaction.

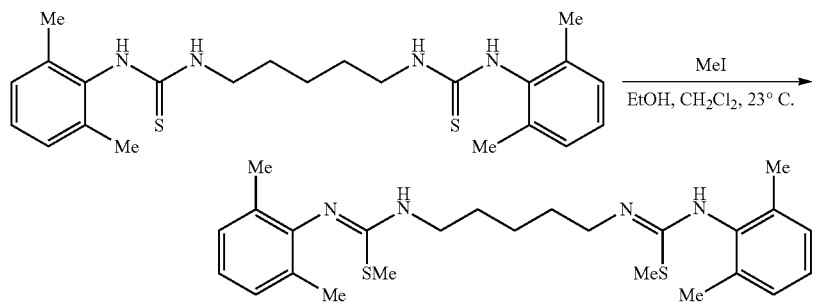

To a solution of the bisthiourea (2.331 g, 5.438 mmol, 1.00 eq) in EtOH—CH$_2$Cl$_2$ (100 mL, 1:1) at 23° C. was added iodomethane (3.087 g, 1.40 mL, 21.752 mmol, 4.00 eq). After stirring (500 rpm) for 12 hrs the clear pale yellow solution was neutralized with a saturated aqueous mixture of NaHCO$_3$ (100 mL), then aqueous NaOH (15 mL, 1 N) was added slowly, the biphasic white heterogeneous mixture was stirred vigorously (1000 rpm) for 2 mins, poured into a separatory funnel, partitioned, organics were washed with a saturated aqueous mixture of NaHCO$_3$ (3×50 mL), residual organics were extracted from the aqueous layer using CH$_2$Cl$_2$ (2×25 mL), combined, washed with brine (1×50 mL), dried over solid Na$_2$SO$_4$, decanted, and concentrated to afford the bismethylisothiourea (2.483 g, 5.438 mmol, 100%). NMR indicates product as a mixture of isomers/tautomers along with minor impurities:

$^1$H NMR (500 MHz, Chloroform-d) δ 7.00 (d, J=7.5 Hz, 4H), 6.86 (t, J=7.5 Hz, 2H), 4.24 (s, 2H), 3.31 (s, 4H), 2.37 (s, 6H), 2.10 (s, 12H), 1.59 (s, 4H), 1.36 (s, 2H).

$^{13}$C NMR (126 MHz, Chloroform-d) δ 152.52, 146.60, 129.25, 127.89, 122.52, 43.01, 29.90, 24.07, 18.01, 13.66.

HRMS (ESI): calc'd C$_{25}$H$_{36}$N$_4$S$_2$[M+11]$^+$ as 457.2454; found 457.3139. The crude material was used in the subsequent reaction without further purification.

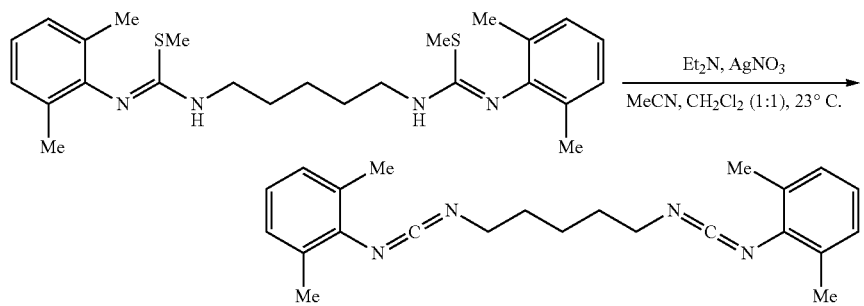

To a stirring (500 rpm) solution of the bismethylisothiourea (2.493 g, 5.459 mmol, 1.00 eq) and Et$_3$N (2.320 g, 3.20 mL, 22.928 mmol, 4.20 eq) in non-anhydrous CH$_2$Cl$_2$-acetonitrile (110 mL, 1:1) in a brown jar protected from light at 23° C. was added solid AgNO$_3$ (3.709 g, 21.836 mmol, 4.00 eq) all at once. After 3.5 hrs the golden brown heterogeneous mixture was diluted with hexanes (100 mL), stirred vigorously (1000 rpm) for 2 mins, suction filtered through a pad of diatomaceous silica, concentrated to ~10 mL, hexanes (50 mL) was added, the mixture was concentrated to ~10 mL, this process was repeated 3× more, hexanes (50 mL) was added, the mixture was suction filtered through a pad of diatomaceous silica, and concentrated to afford the biscarbodiimide as a pale golden yellow oil (1.575 g, 4.370 mmol, 80%). NMR indicates pure product:

$^1$H NMR (500 MHz, Chloroform-d) δ 7.01 (dq, J=7.3, 0.7 Hz, 4H), 6.93 (dd, J=8.2, 6.8 Hz, 2H), 3.40 (t, J=6.8 Hz, 4H), 2.34 (br s, 12H), 1.74-1.66 (m, 4H), 1.59-1.51 (m, 2H).

$^{13}$C NMR (126 MHz, Chloroform-d) δ 136.80, 133.75, 132.19, 128.12, 124.11, 46.67, 30.72, 24.27, 18.93.

HRMS (ESI): calc'd C$_{23}$H$_{28}$N$_4$ [M+H]$^+$ as 361.2314; found 361.2299.

Example 8

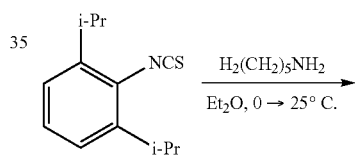

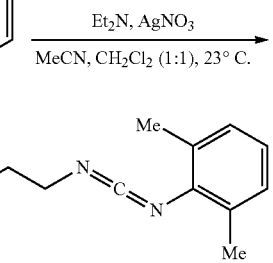

-continued

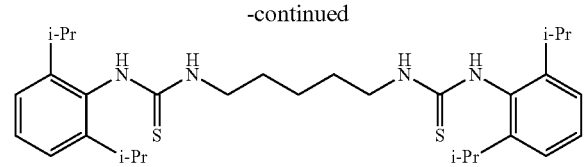

A solution of 2,6-diisopropylphenylisothiocyanate (2.000 g, 1.98 mL, 9.118 mmol, 2.00 eq) in ethyl ether (50 mL) under nitrogen in an oven dried flask was placed in an ice water bath and stirred vigorously (700 rpm) for 30 mins upon which cadaverine (0.466 g, 0.54 mL, 4.559 mmol, 1.00 eq) was added neat. The clear colorless solution instantaneously changed to a white heterogeneous mixture which was allowed to stir for 12 hrs warming gradually to 25° C. in the process. The white mixture was then placed in an ice water bath for 30 mins following which it was suction filtered cold. The white solid was washed with cold ether (3×20 mL) and then dried in vacuo to afford the bisthiourea (1.880 g, 3.476 mmol, 76%). NMR indicates pure product:

$^1$H NMR (400 MHz, DMSO-$d_6$) δ 7.16 (m, 5H), 7.09 (d, J=7.9 Hz, 3H), 4.18 (m, 4H), 3.38-3.16 (m, 4H), 1.43 (p, J=7.3 Hz, 4H), 1.21 (tt, J=8.3, 6.0 Hz, 2H), 1.05 (dd, J=6.5, 0.9 Hz, 24H).

$^{13}$C NMR (101 MHz, DMSO-$d_6$) δ 181.28, 45.11, 43.68, 29.03, 24.29, 22.79.

The product was used in the following reaction.

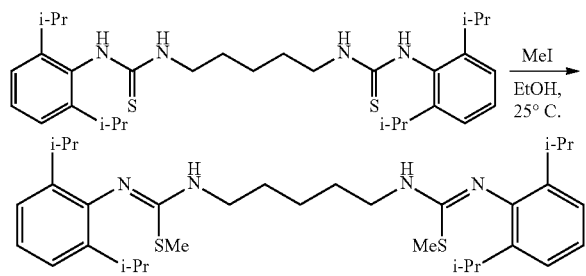

To a solution of the bisthiourea (1.000 g, 1.849 mmol, 1.00 eq) in EtOH (20 mL) was added iodomethane (1.050 g, 0.46 mL, 7.395 mmol, 4.00 eq). The pale yellow solution was allowed to stir (300 rpm) for 12 hrs upon which the clear colorless solution was diluted with an aqueous saturated mixture of NaHCO$_3$ (60 mL), then CH$_2$Cl$_2$ (20 mL), and then aqueous NaOH (20 mL, 1 N). The biphasic mixture was stirred vigorously (1000 rpm) for 2 mins, poured into a separatory funnel, partitioned, the organic layer was washed with an aqueous saturated mixture of NaHCO$_3$ (3×20 mL), residual organics were back extracted from the aqueous layer using CH$_2$Cl$_2$ (3×20 mL), combined, washed with brine (1×20 mL), dried over solid Na$_2$SO$_4$, suction filtered over a pad of Na$_2$SO$_4$, and concentrated to afford the bis-isothiourea as a golden yellow oil (1.031 g, 1.812 mmol, 98%). NMR indicates pure product:

$^1$H NMR (500 MHz, Chloroform-d) δ 7.13 (d, J=8.0 Hz, 4H), 7.05 (dd, J=8.4, 6.8 Hz, 2H), 4.20 (m, 2H), 3.27 (m, 4H), 2.97 (hept, J=6.9 Hz, 4H), 2.44 (br s, 6H), 1.55 (s, 4H), 1.40-1.27 (m, 2H), 1.22 (d, J=6.9 Hz, 12H), 1.18 (d, J=6.9 Hz, 12H).

$^{13}$C NMR (126 MHz, Chloroform-d) δ 153.06, 144.37, 139.53, 123.10, 123.06, 43.03, 30.11, 28.14, 24.04, 23.53, 23.38, 13.59.

ESI-MS: calc'd C$_{33}$H$_{53}$N$_4$S$_2$ [M+H]$^+$ as 569.3721; found 569.3721.

The product is used in the following reaction without further purification.

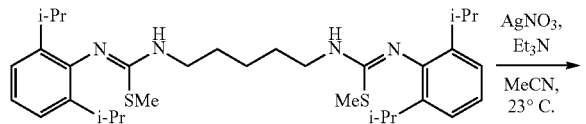

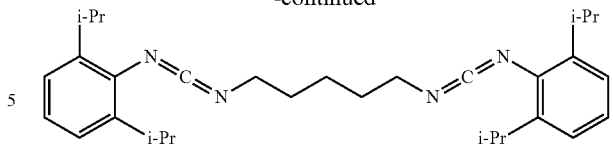

To a solution of the bismethyl isothiourea (1.5956 g, 2.805 mmol, 1.00 eq) and Et$_3$N (1.192 g, 1.64 mL, 11.781 mmol, 4.20 eq) in acetonitrile (30.0 mL) at 23° C. was added solid AgNO$_3$ (1.906 g, 11.220 mmol, 4.00 eq) all at once. After stirring for 3 hrs the yellow heterogeneous mixture was diluted with hexanes (100 mL), stirred vigorously (1000 rpm) for 5 mins, suction filtered cold over a pad of diatomaceous silica with hexanes, and concentrated to ~5 mL. The mixture was diluted with hexanes (20 mL), and concentrated to ~5 mL. This process was repeated twice more, and then the hexanes mixture was suction filtered over a pad of diatomaceous silica using hexanes and concentrated in vacuo to afford the biscarbodiimide (1.212 g, 2.564 mmol, 91%) as a clear golden yellow oil. NMR indicates pure product:

$^1$H NMR (500 MHz, Chloroform-d) δ 7.09 (s, 6H), 3.40 (d, J=6.8 Hz, 4H), 3.38-3.30 (m, 4H), 1.75-1.63 (m, 4H), 1.61-1.47 (m, 2H), 1.24 (d, J=6.9 Hz, 21H).

$^{13}$C NMR (126 MHz, Chloroform-d) δ 142.03, 134.34, 132.65, 124.64, 123.10, 46.54, 30.98, 28.89, 24.28, 23.22.

What is claimed is:

1. A method of synthesizing polycarbodiimides or biscarbodiimides comprising:
   (a) providing an alkylisothiourea of formula (1) to a reaction mixture;

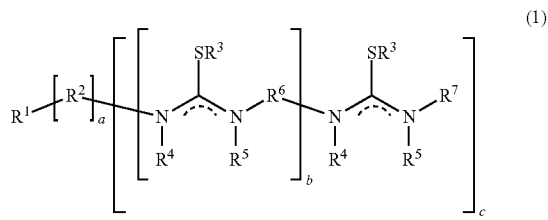

where:
R$^1$=H; (C$_1$-C$_{40}$)hydrocarbyl;
R$^2$=(C$_1$-C$_{40}$)hydrocarbyl;
R$^3$=H; (C$_1$-C$_{40}$)hydrocarbyl;
R$^4$=H; or absent;
R$^5$=H; or absent;
R$^6$=(C$_1$-C$_{40}$)alkyl;
R$^7$=H; (C$_1$-C$_{40}$)hydrocarbyl;
a is 0 or 1;
b is from 1 to 10; and
c is from 1 to 10;
   (b) providing a thiophilic reagent to the reaction mixture and reacting under conditions sufficient to provide the polycarbodiimide or the biscarbodiimide, wherein the thiophilic reagent comprises halide, amine, nitrile, triflate, nitrate, acetate, acetylacetonate, carbonate, oxalate, oxide, phosphate, sulfite, sulfate of copper, zinc, gold, molybdenum, mercury, tungsten, nickel, silver, iron, cobalt, or manganese.

2. The method of synthesizing carbodiimides of claim 1, wherein the reaction mixture further comprises a solvent selected from the list consisting of acetonitrile, proprionitrile, butyronirile, isobutyronitrile, valeronitrile, hexanenitrile, trimethylacetonitrile, malonitrile, succionitrile, glutaronitrile, adiponitrile, 1,5-dicyanopentane, 1,6-dicyanohexane, N,N-dimethylformamide, N,N-dimethyl acetamide, acetone, methylene chloride, 1,2-dichloroethane, chloroform, carbontetrachloride, 1,4-dioxane, benzene, toluene, xylenes, pentane, hexanes, heptanes, petroleum ether, diethyl ether, tetrahydrofuran, 2-methyltetrahydrofuran, methyl-t-butyl ether, or a mixture thereof.

3. The method of synthesizing carbodiimides of claim 1, wherein the reaction mixture further comprises a base selected from the list consisting of acyclic or cyclic N,N,N-trisubstituted amine.

4. The method of synthesizing carbodiimides of claim 1, wherein the reaction mixture has an operating temperature of from −78 to 50° C.

5. The method of synthesizing carbodiimides of claim 1, wherein the thiophilic reagent comprises a metal that is not an alkali metal.

6. The method of synthesizing carbodiimides of claim 1, wherein the thiophilic reagent comprises a metal that is a transition metal.

7. The method of synthesizing carbodiimides of claim 1, wherein the thiophilic reagent is selected from the group consisting of a halide, amine, nitrile, triflate, nitrate, acetate, acetylacetonate, carbonate, oxalate, oxide, phosphate, sulfite, or sulfate of silver.

8. The method of synthesizing carbodiimides of claim 1, wherein the thiophilic reagent is silver nitrate.

* * * * *